United States Patent
Niewöhner et al.

(10) Patent No.: US 6,573,263 B2
(45) Date of Patent: Jun. 3, 2003

(54) SUBSTITUTED IMIDAZOTRIAZINONES

(75) Inventors: Ulrich Niewöhner, Wermelskirchen (DE); Dagmar Schauss, Wuppertal (DE); Martin Hendrix, Odenthal (DE); Gerhard König, Düsseldorf (DE); Frank-Gerhard Böss, Wuppertal (DE); Franz-Josef Van Der Staay, Lohmar (DE); Rudy Schreiber, Köln (DE); Karl-Heinz Schlemmer, Wuppertal (DE); Rolf Grosser, Leverkusen (DE)

(73) Assignee: Bayer Aktiengesellschaft, Leverkusan (DE)

( * ) Notice: Subject to any disclaimer, the term of this patent is extended or adjusted under 35 U.S.C. 154(b) by 0 days.

(21) Appl. No.: 10/026,310

(22) Filed: Dec. 21, 2001

(65) Prior Publication Data

US 2002/0198377 A1 Dec. 26, 2002

(30) Foreign Application Priority Data

Dec. 21, 2000 (DE) .......................... 100 64 105

(51) Int. Cl.⁷ .................... C07D 457/04; C07D 253/06; A61K 31/53; A61P 25/28
(52) U.S. Cl. .......................... 514/243; 544/184; 544/182
(58) Field of Search ........................... 544/184; 514/243

(56) References Cited

U.S. PATENT DOCUMENTS 4,278,673 A  7/1981  Hartley et al. .............. 424/249

FOREIGN PATENT DOCUMENTS

| EP | 0771799 | 5/1997 |
| WO | 9840384 | 9/1998 |
| WO | 9924433 | 5/1999 |
| WO | 9967244 | 12/1999 |
| WO | 0012504 | 3/2000 |

OTHER PUBLICATIONS

Sonnenburg, W., Mullaney, P., Beavo, J., "Molecular Cloning of a Cyclic GMP–stimulated Cyclic Nucleotide Phosphodiesterase cDNA", Biol. Chem. 266: 17655–17661 (1991).

Huettner, J., Baughman, R., "Primary Culture of Identified Neurons from the Visual Cortex of Postnatal Rats", J. Neurosci., 6: 3044–3060 (1986).

Ennaceur, A., Meliani, K., "Effects of Physostigmine and Scopolamine on Rats' Performances in Object–recognition and Radial–maze Tests", Psychopharmacology, 109: 321–330 (1992).

Hoey, M., Houslay, M., "Identification and Selective Inhibition of Four Distinct Soluble Forms of Cyclic Nucleotide Phosphodiesterase Activity from Kidney", Biochem. Pharmacol. 40: 193–202 (1990).

Blokland, A., Prickaerts, J., Honig, W., de Vente, J., "State–dependent Impairment in Object Recognition After Hippocampal NOS Inhibition", NueroReport, 9: 4205–4208 (1998).

Lugnier, C., Schoeffter, P., Le Bec, A., Strouthou E., Stoclet, J., "Selective Inhibition of Cyclic Nucleotide Phosphodiesterases of Human, Bovine and Rat Aorta", Biochem. Pharmacol., 35: 1743–1751 (1986).

Beavo, J., Reifsnyder, D., "Primary Sequence of Cyclic Nucleotide Phosphodiesterase Isozymes and the Design of Selective Inhibitors", Trends in Pharmacol. Sci., 11: 150–155 (1990).

Ennaceur, A., Delacour, J., "A New One–trial Test for Neurobiological Studies of Memory in Rats. 1: Behavioral Data", Behav. Brain. Res., 31: 47–59 (1988).

Hagele, G., Haas, A., "Fluorination of 2–oxo–ethane Derivatives with Diethylaminosulfur Trifluoride (DAST)", J. Fluorine Chem., 76: 15–19 (1996).

Kotoris, C., Chen, M., Taylor, S., "Preparation of Benzylic α, α–Difluoronitriles, –tetrazoles, and –sulfonates Via Electrophilic Fluorination", J. Org. Chem., 63: 8052–8057 (1998).

Prickaerts, J., Steinbusch, H., Smits, J., de Vente, J., "Possible Role of Nitric Oxide–cyclic GMP Pathway in Object Recognition Memory: Effects of 7–nitroindazole and Zaprinast", Eur.J. Pharmacol., 337: 125–136 (1997).

Rosman, G., Martins, T., Sonnenburg, W., Beavo, J., Ferguson, K., Loughney, K., "Isolation and Characterization of Human cDNAs Encoding a cGMP–stimulated 3', 5'–cyclic Nucleotide Phosphodiesterase", Gene, 191: 89–95 (1997).

Soderling, S., Beavo, J., "Regulation of cAMP and cGMP Signaling: New Phophodiesterases and New Functions", Curr. Opin. Cell Biol., 12: 174–179 (2000).

Martins, T., Mumby, M., Beavo, J., "Purification and Characterization of a Cyclic GMP–stimulated Cyclic Nucleotide Phosphodiesterase from Bovine Tissues", J. Biol. Chem., 257: 1973–1979 (1982).

Primary Examiner—Richard L. Raymond
Assistant Examiner—Venkataraman Balasubramanian
(74) Attorney, Agent, or Firm—Jerrie L. Chiu

(57) ABSTRACT

The present invention relates to new substituted imidazotriazinones, processes for their preparation, and their use for the production of medicaments, in particular for improving perception, concentration power, learning power and/or memory power.

11 Claims, No Drawings

SUBSTITUTED IMIDAZOTRIAZINONES

The present invention relates to new substituted imidazotriazinones, processes for their preparation, and their use for the production of medicaments, in particular for improving perception, concentration power, learning power and/or memory power.

Phosphodiesterases (PDEs) play an essential role in the regulation of the intracellular cGMP and cAMP levels. Of the previously described phosphodiesterase isoenzyme groups PDE 1 to PDE 10 (Beavo and Reifsnyder *Trends in Pharmacol. Sci.* 1990, 11, 150–155; Sonderling and Beavo *Curr. Opin. Cell Biol.* 2000, 12, 174–179), the PDEs 1, 2, 5, 9 and 10 are mainly responsible for the metabolism of cGMP. On account of the varying distribution of these cGMP-metabolizing PDEs in the tissue, selective inhibitors should raise the cGMP levels in the corresponding tissue, depending on the tissue distribution of the appropriate isoenzyme.

The particular feature of PDE 2 lies in its positive cooperative kinetics with respect to the substrate cGMP. It was postulated that small amounts of cGMP bind to the so-called cGMP-binding domain and thereby bring about activation of the enzyme. By this means, the affinity of the catalytic domain to cGMP and cAMP is also increased (Martins et al. *J. Biol. Chem.* 1982, 257, 1973–1979). Therefore PDE 2 can hydrolyse and thereby also control both second messenger systems by means of small amounts of cGMP.

PDE 2 has been isolated from various tissues, for example from heart, adrenal gland, liver, platelets and in particular brain. In the brain, PDE 2 mRNA is expressed strongly in the cortex, the basal ganglia and in the hippocampus (Sonnenburg et al. *Biol. Chem.* 1991, 266, 17655–17661). The sequence of the human isoform PDE 2A3 was reported by Rosman et al. *Gene* 1997, 191, 89–95. Of the tissues investigated, the expression of PDE 2A was demonstrated strongly therein in the brain and heart and more weakly in liver, skeletal muscle, kidney and pancreas.

U.S. Pat. No. 4,278,673 discloses imidazopyrimidinones having cAMP PDE-inhibitory action for the treatment of asthma and bronchitis.

WO-A-99/67244 and WO-A-99/24433 disclose 7-alkyl-2-phenyl-imidazotriazinones having PDE 5-inhibiting action for the treatment of vascular diseases.

EP-A-0 771 799, WO-A-98/40384 and WO-A-00/12504 describe purinone, allopurinol and triazolopyrimidinone derivatives, their inhibitory action on cGMP-metabolizing PDEs and their suitability for the treatment of vascular diseases.

The present invention relates to compounds of the general formula (I),

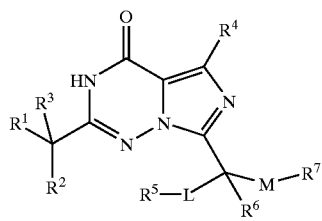

(I)

in which
R$^1$ denotes phenyl, naphthyl, quinolinyl or isoquinolinyl, each of which can be substituted up to three times identically or differently by radicals selected from the group consisting of $(C_1-C_4)$-alkyl, $(C_1-C_4)$-alkoxy, halogen, cyano, —NHCOR$^8$, —NHSO$_2$R$^9$, —SO$_2$NR$^{10}$R$^{11}$, —SO$_2$R$^{12}$, and —NR$^{13}$R$^{14}$,
in which
R$^8$, R$^{10}$, R$^{11}$, R$^{13}$ and R$^{14}$ independently of one another are hydrogen or $(C_1-C_4)$-alkyl, and
R$^9$ and R$^{12}$ independently of one another are $(C_1-C_4)$-alkyl, or
R$^{10}$ and R$^{11}$ together with the adjacent nitrogen atom form an azetidin-1-yl, pyrrol-1-yl, piperid-1-yl, azepin-1-yl, 4-methyl-piperazin-1-yl or morpholin-1-yl radical, or
R$^{13}$ and R$^{14}$ together with the adjacent nitrogen atom form an azetidin-1-yl, pyrrol-1-yl, piperid-1-yl, azepin-1-yl, 4-methyl-piperazin-1-yl or morpholin-1-yl radical,
R$^2$ and R$^3$ independently of one another denote hydrogen or fluorine,
R$^4$ denotes $(C_1-C_4)$-alkyl,
R$^5$ denotes $(C_1-C_3)$-alkyl,
R$^6$ denotes hydrogen or methyl,
R$^7$ denotes phenyl, thiophenyl, furanyl, each of which can be substituted up to three times identically or differently by radicals selected from the group consisting of $(C_1-C_4)$-alkyl, $(C_1-C_4)$-alkoxy, halogen and cyano, or $(C_5-C_8)$-cycloalkyl,
L denotes carbonyl or hydroxymethanediyl, and
M denotes $(C_2-C_5)$-alkanediyl, $(C_2-C_5)$-alkenediyl or $(C_2-C_5)$-alkinediyl,
and their physiologically tolerable salts.

$(C_1-C_4)$-Alkyl and $(C_1-C_3)$-alkyl in the context of the invention represent a straight-chain or branched alkyl radical having 1 to 4 and 1 to 3 carbon atoms respectively. Examples which may be mentioned are: methyl, ethyl, n-propyl, isopropyl, i-, s-, t-butyl. Methyl and ethyl are preferred.

$(C_2-C_5)$-Alkanediyl in the context of the invention represents a straight-chain or branched alkanediyl radical having 2 to 5 carbon atoms. Examples which may be mentioned are ethylene, propane-1,3-diyl, propane-1,2-diyl, propane-2,2-diyl, butane-1,3-diyl, butane-2,4-diyl, pentane-2,4-diyl. A straight-chain $(C_2-C_5)$-alkane-1,ω-diyl radical is preferred. Examples which may be mentioned are ethylene, propane-1,3-diyl, butane-1,4-diyl, pentane-1,5-diyl. Propane-1,3-diyl and butane-1,4-diyl are particularly preferred.

$(C_2-C_5)$-Alkenediyl in the context of the invention represents a straight-chain or branched alkenediyl radical having 2 to 5 carbon atoms. Examples which may be mentioned are ethene-1,2-diyl, ethene-1,1-diyl, propene-1,1-diyl, propene-1,2-diyl, prop-2-ene-1,3-diyl, propene-3,3-diyl, propene-2,3-diyl, but-2-ene-1,4-diyl, pent-2-ene-1,4-diyl. A straight-chain $(C_2-C_5)$-alkene-1,ω-diyl radical is preferred. Examples which may be mentioned are ethene-1,2-diyl, prop-2-ene-1,3-diyl, but-2-ene-1,4-diyl, but-3-ene-1,4-diyl, pent-2-ene-1,5-diyl, pent-4-ene-1,5-diyl. Prop-2-ene-1,3-diyl, but-2-ene-1,4-diyl and but-3-ene-1,4-diyl are particularly preferred.

$(C_2-C_5)$-Alkinediyl in the context of the invention represents a straight-chain or branched alkinediyl radical having 2 to 5 carbon atoms. Examples which may be mentioned are ethine-1,2-diyl, ethine-1,1-diyl, prop-2-ine-1,3-diyl, prop-2-ine-1,1-diyl, but-2-ine-1,4-diyl, pent-2-ine-1,4-diyl. A straight-chain $(C_2-C_5)$-alkene-1,ω-diyl radical is preferred. Examples which may be mentioned are ethine-1,2-diyl, prop-2-ine-1,3-diyl, but-2-ine-1,4-diyl, but-3-ine-1,4-diyl, pent-2-ine-1,5-diyl, pent-4-ine-1,5-diyl. Prop-2-ine-1, 3-diyl, but-2-ine-1,4-diyl and but-3-ine-1,4-diyl are particularly preferred.

$(C_1-C_4)$-Alkoxy in the context of the invention represents a straight-chain or branched alkoxy radical having 1 to 4 carbon atoms. Examples which may be mentioned are: methoxy, ethoxy, n-propoxy, isopropoxy, t-butoxy, n-pentoxy and n-hexoxy. Methoxy and ethoxy are preferred.

$(C_5-C_8)$-Cycloalkyl in the context of the invention represents cyclopentyl, cyclohexyl, cycloheptyl or cyclooctyl. The following may preferably be mentioned are: cyclopentyl, cyclohexyl or cycloheptyl.

Halogen in the context of the invention in general represents fluorine, chlorine, bromine and iodine. Fluorine, chlorine and bromine are preferred. Fluorine and chlorine are particularly preferred.

Preferred salts in the context of the invention are physiologically acceptable salts of the compounds according to the invention.

Physiologically acceptable salts of the compounds according to the invention can be acid addition salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Salts which may be mentioned are, however, also salts with customary bases, such as, for example, alkali metal salts (e.g. sodium or potassium salts), alkaline earth metal salts (e.g. calcium or magnesium salts) or ammonium salts derived from ammonia or organic amines such as, for example, diethylamine, triethylamine, ethyldiisopropylamine, procaine, dibenzylamine, N-methylmorpholine, dihydroabietylamine, 1-ephenamine or methyl-piperidine.

The compounds according to the invention can exist in stereoisomeric forms, which either behave as image and mirror image (enantiomers), or which do not behave as image and mirror image (diastereomers). The invention relates both to the enantiomers and diastereomers or their respective mixtures. Like the diastereomers, the racemic forms can be separated into the stereoisomerically uniform constituents in a known manner.

Preferred compounds of the general formula (I) are those where $R^1$ denotes phenyl whose meta and/or para positions are substituted up to three times identically or differently by radicals selected from the group consisting of $(C_1-C_4)$-alkyl, $(C_1-C_4)$-alkoxy and $-SO_2NR^{10}R^{11}$, and $R^2$, $R^3$, $R^4$, $R^5$, $R^6$, $R^7$, $R^{10}$, $R^{11}$, L and M have the meaning indicated above.

The meta and para positions of the phenyl ring are understood as meaning those positions which are meta or para to the $CR^2R^3$ group. These positions can be illustrated by the following structural formula (Ic):

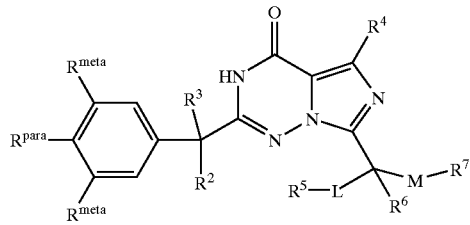

Particularly preferred compounds of the general formula (Ic) are those in which the para and one meta position of the phenyl radical are substituted, and the second meta position is unsubstituted.

Likewise, preferred compounds of the general formula (I) are those where $R^7$ denotes phenyl and $R^1$, $R^2$, $R^3$, $R^4$, $R^5$, $R^6$, L and M have the meaning indicated above.

Very particularly preferred are compounds of the general formula (I), where $R^1$ denotes phenyl, whose meta and/or para positions are substituted up to three times identically or differently by radicals selected from the group consisting of $(C_1-C_4)$-alkyl, $(C_1-C_4)$-alkoxy and $-SO_2NR^{10}R^{11}$, naphthyl or quinolinyl,
in which $R^{10}$ and $R^{11}$ independently of one another are hydrogen or $(C_1-C_4)$-alkyl, $R^1$ and $R^2$ denote hydrogen, $R^4$ denotes methyl or ethyl, $R^5$ denotes methyl, $R^6$ denotes hydrogen or methyl, L denotes carbonyl or hydroxymethanediyl, and M denotes straight-chain $(C_2-C_5)$-alkane-1,ω-diyl, straight-chain $(C_2-C_5)$-alkene-1,ω-diyl or straight-chain $(C_2-C_5)$-alkine-1,ω-diyl.

A further aspect of the invention relates to a new preparation process for the compounds of the general formula (I), in which $R^1$, $R^2$, $R^3$, $R^4$, $R^5$, $R^6$, $R^7$, L and M have the meaning indicated above, where

[A] a compound of the general formula (IIa),

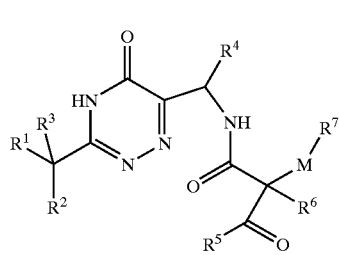

in which $R^1$, $R^2$, $R^3$, $R^4$, $R^5$, $R^6$, $R^7$ and M have the meaning indicated in Claim 1, is reacted under suitable condensation conditions to give a compound of the general formula (Ia),

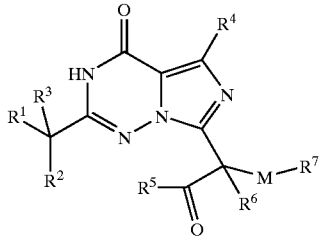

(Ia)

in which $R^1$, $R^2$, $R^3$, $R^4$, $R^5$, $R^6$, $R^7$ and M have the meaning, indicated in Claim 1,
and then, if appropriate,
[B] is reduced under suitable conditions to give a compound of the general formula (Ib)

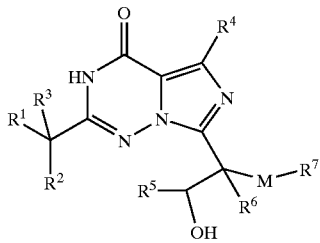

(Ib)

in which $R^1$, $R^2$, $R^3$, $R^4$, $R^5$, $R^6$, $R^7$ and M have the meaning indicated in Claim 1.

The condensation according to reaction step [A] can be carried out by heating the compounds of the general formula (IIa) in the absence of a solvent or in the presence of an inert solvent, in particular of a solvent of the type which forms an azeotropic mixture with water, such as, for example, toluene or xylene, if appropriate in the presence of an acid catalyst and/or of a dehydrating agent. A suitable acid catalyst is, for example, hydrogen chloride and a dehydrating agent which can be used is, for example, acetyl chloride, phosphorus pentoxide or phosphoryl chloride. The condensation is preferably carried out in an inert solvent in the presence of 1–10, preferably 3–7, equivalents of phosphoryl chloride (cf. Chem. Ind. 1983, 331–335).

Suitable inert solvents for the condensation are the customary organic solvents which do not change under the reaction conditions. These include, for example, ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethane, trichloroethylene or chlorobenzene, or ethyl acetate, dimethylformamide, hexamethylphosphoramide, acetonitrile, acetone, dimethoxyethane or pyridine. It is likewise possible to use mixtures of the solvents mentioned. 1,2-Dichloroethane is preferred.

The reaction temperature can be varied within a relatively wide range. In general, the reaction is carried out in a range from −20° C. to 200° C., preferably from −20° C. to 90° C.

The process steps according to the invention are in general carried out at normal pressure. However, it is also possible to work at elevated pressure or at reduced pressure (e.g. in a range from 0.5 to 5 bar).

The reduction according to reaction step [B] can be carried out according to customary methods.

The reductions are in general carried out using hydrides or using boranes, diboranes or their complex compounds in inert solvents.

The reductions can also be carried out by means of hydrogen in water or in inert solvents such as alcohols, ethers or halogenohydrocarbons, or their mixtures, using catalysts such as Raney nickel, palladium, palladium on active carbon or platinum.

Preferably, the reductions are carried out using hydrides, such as complex borohydrides or aluminium hydrides. Particularly preferably, sodium borohydride, lithium borohydride, sodium cyanoborohydride, lithium aluminium hydride, sodium bis(2-methoxyethoxy)aluminium hydride or borane/tetrahydrofuran are employed here.

Suitable solvents here for the reduction are all solvents which do not change under the reaction conditions. These preferably include alcohols such as methanol, ethanol, n-propanol or isopropanol, or ethers such as diethyl ether, dioxane, tetrahydrofuran, glycol dimethyl ether, diethylene glycol dimethyl ether or amides such as hexamethylphosphoramide or dimethylformamide, or acetic acid. It is likewise possible to use mixtures of the solvents mentioned.

The reduction is in general carried out in a temperature range from −50° C. up to the respective boiling point of the solvent, preferably from −20° C. to +90° C., particularly preferably from −5° C. to 30° C.

If necessary, the compounds of the general formula (I) can be separated into the pure diastereomers and/or pure enantiomers. For example, chromatographic separation under normal-, medium- or high-pressure conditions on stationary phases such as, for example, silica gel or reversed phase-modified silica gels or chirally modified silica gels is suitable for this purpose. This is preferably carried out by the high-performance liquid chromatography (=HPLC) method using chiral stationary silica gel phases. Chiral polyamide/silica gel phases based on the monomers N-methacryloyl-L-leucine-d-menthylamide or N-methacryloyl-L-leucine-1-menthylamide are particularly suitable for the separation of the racemates (cf. EP-A-0 379 917).

It can also prove favourable to employ diastereomerically and/or enantiomerically pure compounds of the general formula (IIa) in reaction step [A] and/or to separate the compounds of the general formula (Ia) into the pure diastereomers and/or enantiomers, if appropriate, before carrying out reaction step [B].

It is likewise possible to carry out the reduction [B] diastereoselectively. For this purpose, the reduction is expediently carried out using hydrides, such as complex borohydrides or aluminium hydrides and also boranes in the presence of metal salts. Particularly preferred metal salts are those whose cations are capable of bidentate coordination, such as, for example, metals of the main groups IIa and IIIa or metals of the subgroups including the lanthanoids. Salts of Zn, Mn, Mg or Ca are particularly preferred. Anions which can be used are, for example, halides or acetates. The reaction is expediently carried out in an alcohol or a mixture of an alcohol and a further inert solvent. Mixtures of methanol or ethanol and dichloromethane are preferred. The reduction is in general carried out in a temperature range from −50° C. up to the respective boiling point of the solvent, preferably from −20° C. to +90° C., particularly preferably from −5° C. to 30° C.

The reduction is carried out, inter alia, using 1 to 20 equivalents of the reducing agent in the presence of 0.1 to 10 equivalents of metal salt. In a preferred embodiment, 0.2 to 3 equivalents of metal salt are used. Preferred reducing agents are, for example, sodium borohydride, lithium borohydride, sodium cyanoborohydride or zinc borohydride.

The intermediates of the general formula (II) are new.

A further aspect of the present invention therefore relates to the new compounds of the general formula (II),

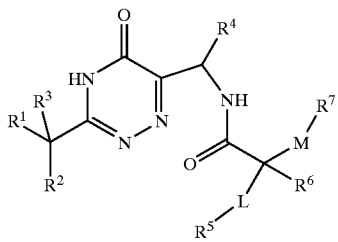

(II)

in which $R^1$, $R^2$, $R^3$, $R^4$, $R^5$, $R^6$, $R^7$, L and M have the meaning indicated above,
and their salts.

The compounds of the general formula (IIa) can be prepared, for example, according to known methods by the oxidation of corresponding compounds of the general formula (IIb),

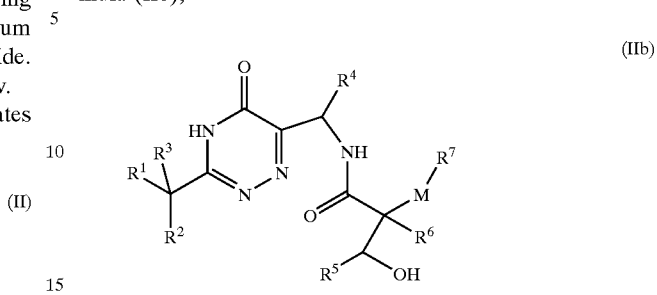

(IIb)

in which $R^1$, $R^2$, $R^3$, $R^4$, $R^5$, $R^6$, $R^7$ and M have the meaning indicated in Claim 1, for example by Swern oxidation or Collins oxidation (for further oxidation methods also see March, J. M., "Advanced Organic Chemistry", 3rd Edition, John Wiley, New York, 1985, pp. 1057–1060 and literature cited therein).

The preparation of the compounds of the general formula (II) can be illustrated by way of example by the following synthesis scheme:

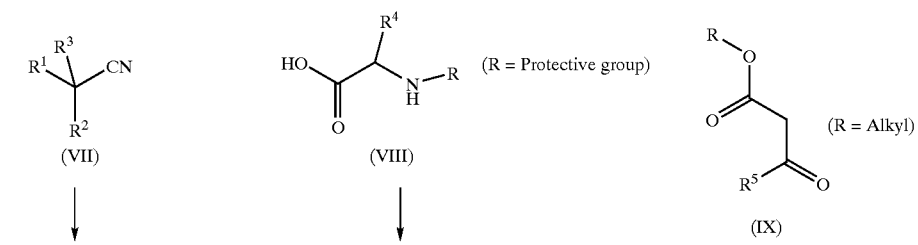

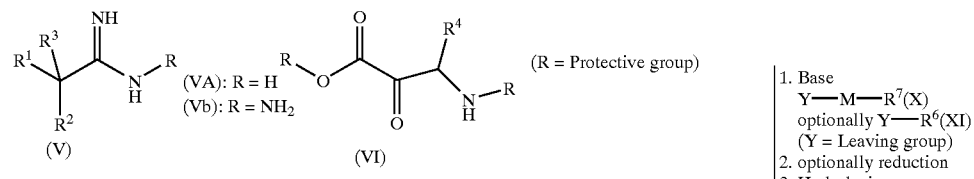

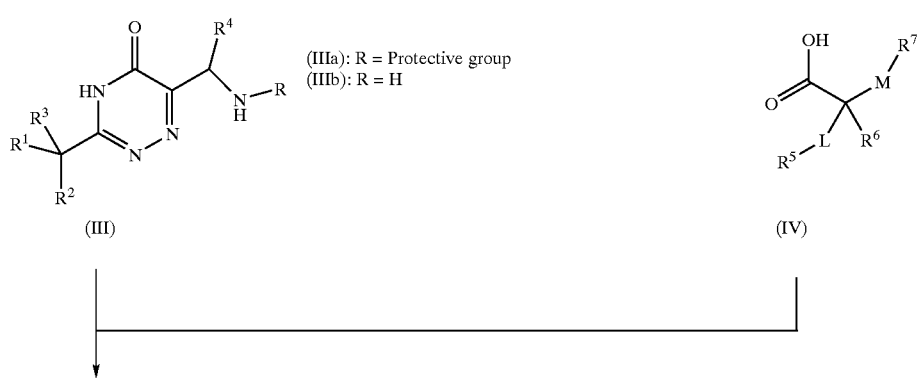

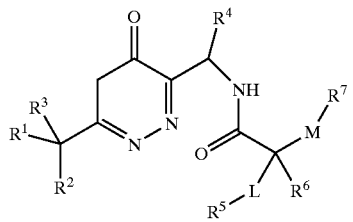

(II)

The compounds of the general formulae (III), (IV), (V), (VI), (VII), (VIII), (IX), (X) and (XI) are known or can be prepared by known processes.

According to this reaction scheme, the aminomethyltriazinones (IIIb) are condensed with the carboxylic acids (IV) under the conditions customary for the formation of amide bonds using a dehydrating reagent in an inert solvent, if appropriate in the presence of a base.

Suitable dehydrating reagents are carbodiimides, such as, for example, diisopropylcarbodiimide, dicyclohexylcarbodiimide (DCC) or N-(3-dimethylaminopropyl)-N'-ethylcarbodiimide hydrochloride (EDC) or carbonyl compounds such as carbonyldiimidazole or 1,2-oxazolium compounds such as 2-ethyl-5-phenyl-1,2-oxazolium-3-sulphonate or propanephosphonic anhydride or isobutyl chloroformate or benzotriazolyloxy-tris-(dimethylamino) phosphonium hexafluorophosphate or diphenyl phosphoramidate or methanesulphonyl chloride, if appropriate in the presence of bases such as triethylamine, N-ethylmorpholine, N-methylmorpholine or N-methylpiperidine, and if appropriate in the presence of a catalyst such as N-hydroxysuccinimide or N-hydroxybenzotriazole (HOBT). The condensation with EDC is preferably carried out in the presence of NMM and HOBT.

Suitable solvents are the customary inert solvents described above. Dichloromethane is preferred.

The aminomethyltriazinones (IIIb) are obtainable by deprotection of the corresponding N-protected aminomethyltriazinones (IIIa), which in turn are accessible via cyclocondensation of the corresponding amidrazones (Vb) and α-keto esters (VI).

Suitable amino protective groups for the intermediates (IIIa), (VI) and (VIII) are, for example, acyl radicals, in particular the acetyl group. These groups can be cleaved into the N-protected aminomethyltriazinones (IIIa) under acidic conditions, for example by heating in hydrochloric acid.

The cyclocondensation to give the N-protected aminomethyltriazinones (IIIa) can be brought about by heating the individual components, the amidrazones (Vb) and α-keto esters (VI), in an alcoholic solvent, preferably by heating to reflux in ethanol.

The amidrazones (Vb) can be prepared by reaction of the corresponding amidines (Va) with, for example, hydrazine hydrate and are either isolated or employed in situ in the following reaction. The amidines (Va) are accessible from the corresponding nitrites (VII) according to customary methods, for example by reaction of the nitrites (VII) with ammonium chloride and a solution of trimethylaluminium in hexane firstly in a temperature range from −20° C. to room temperature, preferably at 0° C. and then at 60 to 100° C., preferably 70 to 90° C., and preferably at normal pressure.

The nitriles (VII) are known or can be prepared according to customary methods. For example, aryl-difluoroacetonitriles can be prepared from arylacetonitriles or aryloxoacetonitriles (cf. *J. Org. Chem.* 1998, 63, 8052–8057 or *J. Fluorine Chem.* 1996, 76, 15–20).

The α-keto esters (VI) can be prepared from the corresponding N-protected α-amino acids (VIII), for example by reaction with ethyl oxalyl chloride.

The carboxylic acids (IV) are accessible by alkylation of the corresponding β-keto esters (IX) with the electrophiles (X) and if appropriate (XI), followed by ester hydrolysis and, if appropriate, reduction of the β-carbonyl function.

For alkylation, the β-ketoester (IX) is deprotonated for example using a base, preferably a hydride such as sodium hydride, in an inert solvent such as, for example, tetrahydrofuran in a temperature range from preferably 0° C. to room temperature and, after isolation or in situ, treated with a solution of the electrophile (X) or (XI) in, preferably, 1,3-dimethyltetrahydro-2-(1H)-pyrimidone with addition of a catalytic amount of potassium iodide. If $R^6$ is not hydrogen, the alkylation can be repeated using a second electrophile after the monoalkylation product has optionally been isolated. The leaving group Y in the electrophile (X) or (XI) is preferably a halogen, particularly preferably bromine.

The β-carbonyl function can be reduced according to the conditions described above for reaction step [B].

The hydrolysis of the ester to the carboxylic acid (IV) is carried out according to customary conditions, in the case of the methyl or ethyl ester preferably using sodium or potassium hydroxide solution.

Substituents, for example in $R^1$, can be introduced via the starting materials, such as, for example, via the nitrile (VII), but can also be introduced or modified in a later process stage.

Thus the substituent $-SO_2NR^{10}R^{11}$, for example, can be introduced into $R^1$ by chlorosulphonating an appropriate N-protected aminomethyltriazinone (IIIa) with chlorosulphonic acid and then further reacting it with an appropriate amine $HNR^{10}R^{11}$ to give the corresponding sulphonamide.

This can be illustrated by the following reaction scheme:

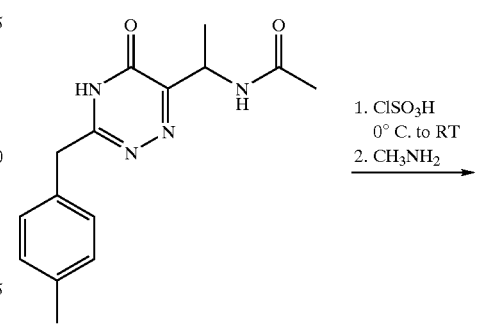

1. ClSO₃H
   0° C. to RT
2. CH₃NH₂

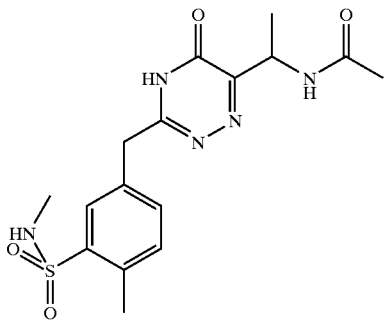

The compounds according to the invention show an unforeseeable, valuable spectrum of pharmacological action: they preferably inhibit PDE 2, and/or exhibit a favourable pharmacokinetic profile.

The inhibition of PDE 2 leads to a differentiated increase in cGMP. The differentiating action is additionally determined by the distribution of the isoenzymes in the tissue.

The compounds according to the invention moreover intensify the action of substances, such as, for example, EDRF (endothelium-derived relaxing factor) and ANP (atrial natriuretic peptide), which increase the cGMP level.

Because of their selective PDE 2 inhibition, the compounds according to the invention are particularly suitable for improving perception, concentration power, learning power or memory power, in particular after cognitive disorders, such as occur, for example, in situations/illnesses/syndromes such as mild cognitive impairment, age-associated learning and memory disorders, age-associated memory losses, vascular dementia, craniocerebral trauma, stroke, dementia which occurs after strokes (post-stroke dementia), post-traumatic craniocerebral trauma, general concentration disorders, concentration disorders in children with learning and memory problems, Alzheimer's disease, vascular dementia, dementia with Lewy bodies, dementia with degeneration of the frontal lobes including Pick's disease, Parkinson's disease, progressive nuclear palsy, dementia with corticobasal degeneration, amyolateral sclerosis (ALS), Huntington's disease, multiple sclerosis, thalamic degeneration, Creutzfeld-Jacob dementia, HIV dementia, schizophrenia with dementia or Korsakoff psychosis.

The compounds according to the invention are generally suitable for the treatment and/or prophylaxis of dementia.

The active compound can act systemically and/or locally. For this purpose, it can be administered in a suitable manner, such as, for example, orally, parenterally, pulmonarily, nasally, sublingually, lingually, buccally, rectally, transdermally, conjunctivally, otically or as an implant.

For these administration routes, the active compound can be administered in suitable administration forms.

For oral administration, known administration forms releasing the active compound rapidly and/or in modified form are suitable, such as, for example, tablets (non-coated and coated tablets, e.g. enteric coatings), capsules, sugar-coated tablets, granules, pellets, powders, emulsions, suspensions and solutions.

The parenteral administration can take place with circumvention of an absorption step (intravenous, intraarterial, intracardiac, intraspinal or intralumbar) or with involvement of an absorption (intramuscular, subcutaneous, intracutaneous, percutaneous, or intraperitoneal). For parenteral administration, suitable administration forms are, inter alia, injection and infusion preparations in the form of solutions, suspensions, emulsions, lyophilizates and sterile powders.

For the other administration routes, for example, inhalation pharmaceutical forms (inter alia powder inhalers, nebulizers), nasal drops/solutions, sprays; tablets or capsules to be applied lingually, sublingually or buccally, suppositories, ear and eye preparations, vaginal capsules, aqueous suspensions (lotions, shake lotions), lipphilic suspensions, ointments, creams, milk, pastes, dusting powder or implants are suitable.

The active compounds can be converted into the administration forms mentioned in a known manner. This takes place using inert non-toxic, pharmaceutically suitable excipients. These include, inter alia, vehicles (e.g. microcrystalline cellulose), solvents (e.g. liquid polyethylene glycols), emulsifiers (e.g. sodium dodecylsulphate), dispersants (e.g. polyvinylpyrrolidone), synthetic and natural biopolymers (e.g. albumin), stabilizers (e.g. antioxidants such as ascorbic acid), colourants (e.g. inorganic pigments such as iron oxides) or taste and/or odour corrigents.

In general, it has proved advantageous in the case of parenteral administration to administer amounts of approximately 0.001 to 30 mg/kg, preferably approximately 0.01 to 10 mg/kg, of body weight to achieve effective results. In the case of oral administration, the amount is approximately 0.01 to 100 mg/kg, preferably approximately 0.1 to 30 mg/kg, of body weight.

In spite of this, it may be necessary, if appropriate, to deviate from the amounts mentioned, namely depending on the body weight, route of application, individual behaviour towards the active compound, manner of preparation and time or interval at which administration takes place.

Measurement of the PDE Inhibition

The cGMP-stimulable PDE (PDE 2), the cGMP-inhibitable PDE (PDE 3) and the cAMP-specific PDE (PDE 4) were isolated either from porcine or bovine heart myocardium. The $Ca^{2+}$ calmodulin-stimulable PDE 1 was isolated from porcine aorta, porcine brain or preferably from bovine aorta. The cGMP-specific PDE (PDE 5) was preferably obtained from porcine small intestine, porcine aorta, human blood platelets and preferably from bovine aorta. Purification was carried out by anion exchange chromatography on mono $Q^R$ Pharmacia essentially according to the method of Hoey, M; Houslay, M. D., *Biochem. Pharmacol.* 1990, 40, 193–202 and Lugman et al. *Biochem. Pharmacol.* 1986, 35, 1743–1751.

The enzyme activity was determined in a test batch of 100 μl in 20 mM tris/HCl buffer pH 7.5 which contains 5 mM $MgCl_2$, 0.1 mg/ml of bovine serum albumin and either 800 Bq of [$^3$H]-cAMP or [$^3$H]-cGMP. The final concentration of the corresponding nucleotides is $10^{-6}$ mol/l. The reaction is started by addition of the enzyme and the amount of enzyme is proportioned such that about 50% of the substrate are reacted during the incubation time of 30 min. In order to test the cGMP-stimulable PDE 2, [$^3$H]-cAMP is used as a substrate and $10^{-6}$ mol/l of non-labelled cGMP is added to the batch. In order to test the Ca calmodulin-dependent PDE 1, additionally $CaCl_2$ 1 μM and calmodulin 0.1 μM and are added to the reaction batch. The reaction is stopped by addition of 100 μl of acetonitrile which contains 1 mM cAMP and 1 mM AMP. 100 μl of the reaction batch are separated on the HPLC and the cleavage products are determined quantitatively online using a flow-through scintillation counter. The substance concentration at which the reaction rate is decreased by 50% is measured. In addition, the phosphodiesterase [$^3$H] cAMP SPA enzyme assay and the phosphodiesterase [$^3$H] cGMP SPA enzyme assay from Amersham Life Sciences were used for testing. The test was carried out according to the experimental protocol indicated by the manufacturer.

The activity of the test substances on PDE 2 was determined using the [$^3$H] cAMP Scintillation Proximity Assay (SPA) kit (TRKQ7090) from Amersham International (Little Chalfont, England) or on PDE1 and PDE5 using the [$^3$H] cGMP Scintillation Proximity Assay (SPA) Kit (TRKQ7100) from Amersham International (Little Chalfont, England).

Test substances were dissolved in 100% DMSO (10 mM), and this solution was further diluted with $H_2O$ (highest final concentration in the test: 10 $\mu$M). For the prestimulation of the PDE 2, cGMP is additionally added (final concentration in the test: $10^{-6}$ M). The enzyme is diluted in PDE buffer (20 mM TRIS/HCl, 5 mM $MgCl_2$, 0.1 mg/ml of albumin, pH 7.5). The following volumes per hole are pipetted into a 96-hole plate (Wallac, 1450–401): 10 $\mu$l of substance solution (at the 100% value 10 $\mu$l of $H_2O$), 10 $\mu$l of cGMP ($10^{-5}$ M), 70 $\mu$l of [$^3$H]-cAMP test mixture (see kit), 10 $\mu$l of enzyme (at the 0 value no enzyme, instead of this +10 $\mu$l of $H_2O$) at the start of the reaction. After incubation at 30° C. for 15 min, the reaction was stopped using 50 $\mu$l of SPA bead solution (see kit), and the plate was sealed with a film and shaken for 30 seconds. After the beads had settled (about 15 min), the plate was measured in a beta counter.

For the measurement of PDE 1, calmodulin $10^{-7}$ M and $CaCl_2$ 1 $\mu$M were added to the reaction batch. The PDE 5 was measured using the [$^3$H] cGMP SPA Assay.

For example, under the conditions indicated above Example 2 inhibits the PDE 2 with an $IC_{50}$ value of 10 nM.

Measurement of the Increase in the Intracellular Neuronal cGMP Concentration in Cell Cultures PDE 2 inhibitors increase the intracellular neuronal cGMP concentration after prestimulation of the guanylate cyclase using $10^{-4}$ M sodium nitroprusside (SNP) in primary rat brain cell cultures.

Rat embryos were decapitated and the heads were transferred to preparation dishes. The scalp and cranium were removed, and the exposed brains were transferred to a further Petri dish. With the aid of a binocular microscope and two pairs of forceps, hippocampi were isolated from the cortex and cooled to 4° C. using ice. This preparation and the isolation of the hippocampal neurons were then carried out according to a standard protocol using the papain dissociation system (Worthington Biochemical Corporation, Lakewood, N.J. 08701, USA) (Huettner et al. *J. Neurosci.* 1986, 6, 3044–3060). The mechanically isolated neurons were cultured under standard conditions (37° C., 5% $CO_2$) to 150,000 cells/hole in 200 $\mu$l of neurobasal medium/hole (neurobasal; Gibco/BRL; 2 mM L-glutamine; in the presence of penicillin/streptomycin) for 7 days in 96-hole plates (pretreated with poly-D-lysine 100 $\mu$g/ml for 20 min). After 7 days, the medium was removed and the cells were washed with HBS buffer (Gibco/BRL). Subsequently, 100 $\mu$l each of SNP solution and 100 $\mu$l of the racemate of Example 1 (dissolved in 100% DMSO beforehand: 10 mM) were added in HBS to the cells such that the final concentration of SNP was 100 mM and that of the racemate of Example 1 was as indicated in FIG. 1 and the mixture was incubated at 37° C. for 20 min. The cells were then lysed in 200 $\mu$l of lysis buffer (cGMP kit code RPN 226; from Amersham Pharmacia Biotech.) and the cGMP concentration was measured according to the instructions of the manufacturer. All measurements were carried out in triplicate. Statistical analysis was carried out using Prism Software Version 2.0 (GraphPad Software Inc., San Diego, Calif. USA; *** p<0.001).

In the case of parallel incubation of neurons with SNP (a stimulator of guanylate cyclase) and Example 15, a marked increased in the intracellular cGMP level was seen even from a concentration of 100 nM.

Object Recognition Test

The object recognition test is a memory test. It measures the ability of rats (and mice) to differentiate between known and unknown objects and is therefore suitable for the determination of the memory-improving action of the compounds according to the invention.

The test is carried out as described (Blokland et al. *NeuroReport* 1998, 9, 4205–4208; Ennaceur, A., Delacour, J., *Behav. Brain Res.* 1988, 31, 47–59; Ennaceur, A., Meliani, K., *Psychopharmacology* 1992, 109, 321–330; Prickaerts, et al. *Eur. J. Pharmacol.* 1997, 337, 125–136).

In a first passage, a rat in an otherwise empty relatively large observation arena is confronted with two identical objects. The rat will extensively examine, i.e. sniff and touch, both objects. In a second passage, after an interval of 24 hours, the rat is again tested in the observation arena. One of the known objects is now replaced by a new, unknown object. When a rat recognizes the known object, it will especially examine the unknown object. After 24 hours, a rat, however, has normally forgotten which object it has already examined in the first passage, and will therefore inspect both objects equally intensively. The administration of a substance having learning- and memory-improving action will lead to a rat recognizing the object already seen 24 hours beforehand, in the first passage, as known. It will examine the new, unknown object in greater detail than the already known one. This memory power is expressed in a discrimination index. A discrimination index of zero means that the rat examines both objects, the old and the new one, for the same length of time; i.e. it has not recognized the old object and reacts to both objects as if they were both unknown and new. A discrimination index of greater than zero means that the rat has inspected the new object for longer than the old one; i.e. the rat has recognized the old object.

Under these conditions, Example 16 shows an effect at a dose of 1.0 mg/kg of body weight p.o.

Definitions of Terms

Chromatography, if not mentioned otherwise, was carried out on silica gel Si 60. In the case of flash chromatography, the described conditions were normally followed (cf. Still J. Org. Chem.).

If not described otherwise, the reactions were carried out under argon and, where necessary, under anhydrous conditions.

HPLC=high-pressure liquid chromatography

MS=mass spectrometry

NMR=nuclear magnetic resonance spectroscopy

LC-MS=liquid chromatography combined with mass spectrometry

MeOH=methanol

DMSO=dimethyl sulphoxide of th.=of theory

Starting Compounds

EXAMPLE 1A

N-Acetylalanine

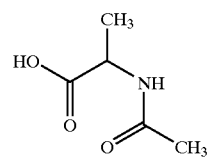

134 g (1.50 mol) of DL-alanine are introduced into acetic acid and treated dropwise with 230 g (2.25 mol) of acetic anhydride. The mixture is additionally stirred at 100° C. for 2 h to complete the reaction and the solvent is then stripped off in vacuo. The solid obtained is suspended in ethyl acetate and filtered off with suction. For purification, the solid is washed several times with diethyl ether.

Yield: 162 g (82.6% of th.)

$^1$H-NMR (methanol-d$_4$): δ/ppm 1.38 (d, 3H), 1.97 (s, 3H), 4.37 (q, 1H).

EXAMPLE 2A 2-(Acetylamino)butanoic Acid

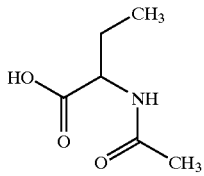

163 g (1.58 mol) of 2-aminobutyric acid are reacted analogously to Example 1A with 242 g (2.37 mol) of acetic anhydride to give 2-(acetylamino)butanoic acid.

Yield: 220 g (95.9% of th.)

$^1$H-NMR (methanol-d$_4$): δ/ppm 0.97 (t, 3H), 1.65–1.93 (m, 2H), 1.99 (s, 3H), 4.29 (q, 1H).

EXAMPLE 3A 2-(4-Methylphenyl)ethanamidine Hydrochloride

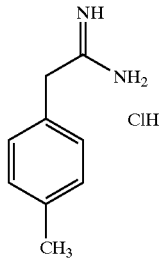

10.8 g (201 mmol) of ammonium chloride are suspended under argon in 200 ml of dry toluene and the suspension is cooled to 0° C. 100 ml of a 2M solution of trimethylaluminium in hexane are added dropwise and the mixture is stirred at room temperature until the evolution of gas is complete. After addition of 13.2 g (100 mmol) of 4-methylbenzyl cyanide, the reaction mixture is stirred overnight at 80° C. (bath). The cooled reaction mixture is treated with 35 ml of methanol and then stirred at room temperature for a further 1 h. The solid is then first filtered off with suction, and the filter cake is washed several times with methanol. The filtrate is concentrated, resuspended in dichloromethane/methanol 10/1, and the insoluble solid is filtered off. The solvent is then again evacuated from the filtrate in vacuo.

Yield: 16.4 g (88.1% of th.)

$^1$H-NMR (methanol-d$_4$): δ/ppm 2.35 (s, 3H), 3.77 (s, 2H), 7.21–7.29 (m, 4H).

EXAMPLE 4A 2-(4-Methoxyphenyl)ethanamidine Hydrochloride

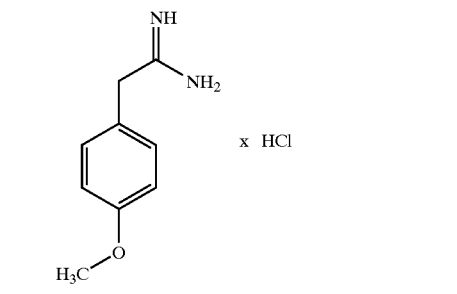

Analogously to Example 3A, starting from 21.4 g (400 mmol) of ammonium chloride, 200 ml of a 2M solution of trimethylaluminium in hexane and 29.4 g (200 mmol) of 4-methoxybenzyl cyanide, 28.5 g (71.3% of th.) of 2-(4-methoxyphenyl)ethanamidine hydrochloride are obtained.

Melting point: 126° C.

EXAMPLE 5A 2-(3,4-Dimethoxyphenyl)ethanamidine Hydrochloride

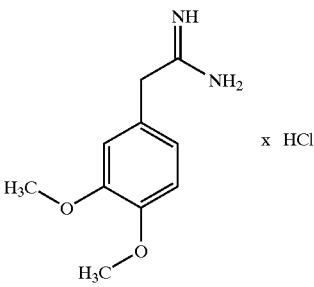

Analogously to Example 3A, starting from 72.5 g (1.35 mol) of ammonium chloride, 672 ml of a 2M solution of trimethylaluminium in hexane and 120 g (677 mmol) of 3,4-dimethoxybenzyl cyanide, 112 g (71.7% of th.) of 2-(3, 4-dimethoxyphenyl)ethanamidine hydrochloride are obtained.

$^1$H-NMR (DMSO-d$_6$): δ/ppm 3.62 (s, 2H), 3.74 (s, 3H), 3.76 (s, 3H), 6.92–7.14 (m, 3H).

EXAMPLE 6A 2-(3-Ethoxy-4-methoxyphenyl)ethanamidine Hydrochloride

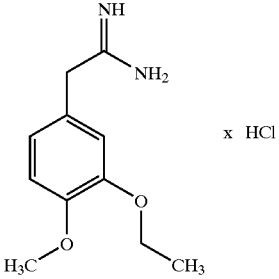

Analogously to Example 3A, starting from 5.59 g (105 mmol) of ammonium chloride, 52.1 ml of a 2M solution of trimethylaluminium in toluene and 10 g (52.3 mmol) of 3-ethoxy-4-methoxybenzyl cyanide, 3.8 g (29.7% of th.) of 2-(3-ethoxy-4-methoxyphenyl)ethanamidine hydrochloride are obtained.

$^1$H-NMR (DMSO-d$_6$): δ/ppm 1.34 (t, 3H), 3.59 (s, 2H), 3.73 (s, 3H), 4.02 (q, 2H), 6.92–7.12 (m, 3H).

EXAMPLE 7A 2-(1-Naphthyl)ethanamidine Hydrochloride

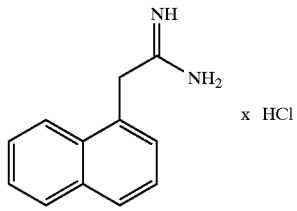

Analogously to Example 3A, starting from 32.9 g (614 mmol) of ammonium chloride, 307 ml of a 2M solution of trimethylaluminium in toluene and 51.4 g (307 mmol) of 1-naphthylacetonitrile, 56.3 g (83.1% of th.) of 2-(1-naphthyl)ethanamidine hydrochloride are obtained.

$^1$H-NMR (DMSO-d$_6$): δ/ppm 4.28 (s, 2H), 7.48–8.06 (m, 7H).

EXAMPLE 8A 2-(6-Quinolinyl)ethanamidine Hydrochloride

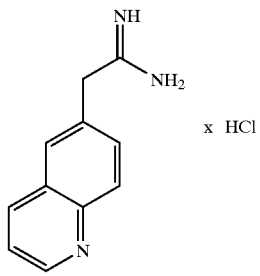

21.4 g (400 mmol) of ammonium chloride are suspended in 400 ml of dry toluene and the suspension is cooled to 0° C. 200 ml of a 2M solution of trimethylaluminium in toluene are added dropwise and the mixture is stirred at room temperature until the evolution of gas is complete. After addition of 17.9 g (88.9 mmol) of methyl 6-quinolinylacetate, the reaction mixture is stirred overnight at 100° C. (bath). The cooled reaction mixture is treated with 90 g of silica gel and then stirred at room temperature for a further 15 min. The solid is then filtered off with suction, and the filter cake is washed several times more with dichloromethane/methanol 10/1. The filtrate is concentrated.

$^1$H-NMR (DMSO-d$_6$): δ/ppm 3.97 (s, 2H), 7.54–9.31 (m, 6H).

EXAMPLE 9A

Ethyl 3-(acetylamino)-2-oxobutanoate

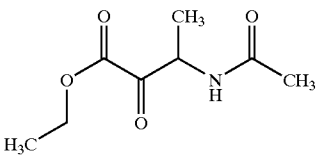

10.65 g (81.2 mmol) of acetylalanine are taken up in 150 ml of tetrahydrofuran and heated under reflux with 19.3 g (244 mmol) of pyridine and a spatula tipful of N,N-dimethylaminopyridine. At boiling heat, 22.2 g (162 mmol) of ethyl oxalyl chloride are added dropwise. The mixture is then heated at reflux until the evolution of gas can no longer be observed. After cooling, the batch is added to ice water and the organic phase is extracted in ethyl acetate. The dried organic phase is concentrated and, dissolved directly in ethanol, reacted further.

EXAMPLE 10A

N-{1-[3-(4-Methylbenzyl)-5-oxo-4,5-dihydro-1,2,4-triazin-6-yl]ethyl}acetamide

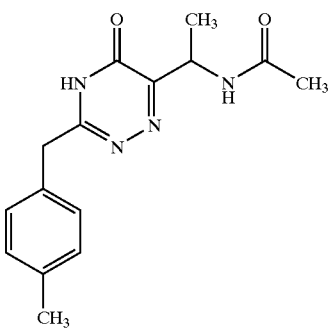

10 g (54.2 mmol) of 2-(4-methylphenyl)ethanamidine hydrochloride are taken up in 100 ml of ethanol and treated with 3.25 g (65.0 mmol) of hydrazine hydrate. The mixture is stirred for 45 min, then Example 9A is added. It is then stirred for 4 h at 80° C. (bath) and overnight at room temperature. The substance is purified by flash chromatography, preliminary fractions first being separated off using ethyl acetate. The product is eluted with dichloromethane/methanol 30/1.

Yield: 5.63 g (36.3% of th.)

$^1$H-NMR (methanol-d$_4$): δ/ppm 1.40 (d, 3H), 1.93 (s, 3H), 2.29 (s, 3H), 3.85 (s, 2H), 5.12 (q, 1H), 7.12–7.23 (m, 4H).

EXAMPLE 11A 6-(1-Aminoethyl)-3-(4-methylbenzyl)-1,2,4-triazin-5(4H)-one

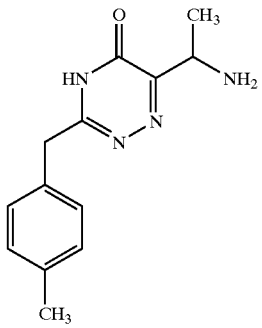

20 g (69.9 mmol) of N-{1-[3-(4-methylbenzyl)-5-oxo-4,5-dihydro-1,2,4-triazin-6-yl]-ethyl}acetamide are stirred under reflux in 200 ml of 2 N hydrochloric acid for 18 h. The cooled mixture is then neutralized using 6 N NaOH and evaporated to dryness in vacuo. The residue is suspended in methanol and the salt is separated off. The concentrated filtrate is flash-chromatographed using dichloromethane/methanol 20/1 and 5/1.

Yield: 8 g (46.9% of th.)

$^1$H-NMR (methanol-d$_4$): δ/ppm 1.50 (d, 3H), 2.20 (s, 3H), 3.84 (s, 2H), 4.52 (q, 1H), 7.03 (d, 2H), 7.13 (d, 2H).

EXAMPLE 12A

N-{1-[3-(4-Methoxybenzyl)-5-oxo-4,5-dihydro-1,2,4-triazin-6-yl]ethyl}acetamide

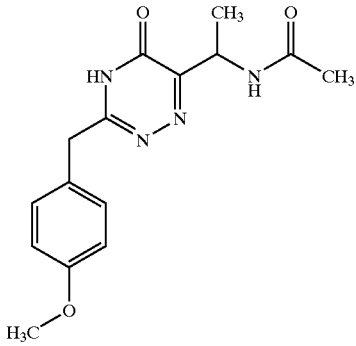

Analogously to Example 10A, 5.1 g (25.4 mmol) of 2-(4-methoxyphenyl)ethanamidine hydrochloride are reacted with 1.53 g (30.5 mmol) of hydrazine hydrate and 7.14 g (38.1 mmol) of ethyl 3-(acetylamino)-2-oxobutanoate to give N-{1-[3-(4-methoxybenzyl)-5-oxo-4,5-dihydro-1,2,4-triazin-6-yl]ethyl}acetamide.

Yield: 2.97 g (38.7% of th.)

$^1$H-NMR (methanol-d$_4$): δ/ppm 1.44 (d, 3H), 1.99 (s, 3H), 3.78 (s, 3H), 3.91 (s, 2H), 5.23 (q, 1H), 6.90 (d, 2H), 7.28 (d 2H).

EXAMPLE 13A 6-(1-Aminoethyl)-3-(4-methoxybenzyl)-1,2,4-triazin-5(4H)-one

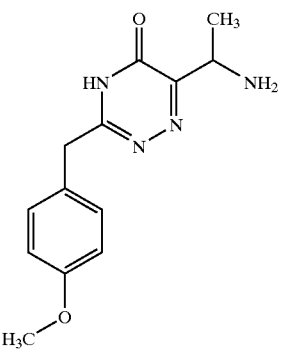

Analogously to Example 11A, 17 g (56.2 mmol) of N-{1-[3-(4-methoxybenzyl)-5-oxo-4,5-dihydro-1,2,4-triazin-6-yl]ethyl}acetamide are reacted to give 6-(1-aminoethyl)-3-(4-methoxybenzyl)-1,2,4-triazin-5(4H)-one.

Yield: 5 g (34.2% of th.)

$^1$H-NMR (methanol-d$_4$): δ/ppm 1.55 (d, 3H), 3.74 (s, 3H), 3.84 (s, 2H), 4.51 (q, 1H), 6.83 (d, 2H), 7.24 (d, 2H).

EXAMPLE 14A

N-{1-[3-(3,4-Dimethoxybenzyl)-5-oxo-4,5-dihydro-1,2,4-triazin-6-yl]ethyl}acetamide

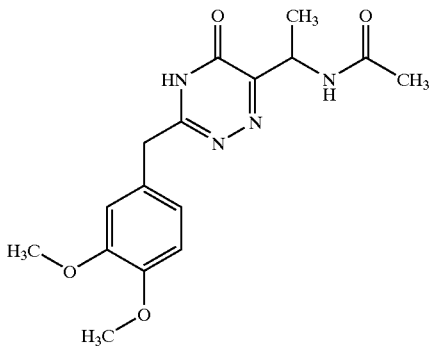

Analogously to Example 10A, 20.0 g (86.7 mmol) of 2-(3,4-dimethoxyphenyl)ethanamidine hydrochloride are reacted with 5.21 g (104 mmol) of hydrazine hydrate and 24.3 g (130 mmol) of ethyl 3-(acetylamino)-2-oxobutanoate to give N-{1-[3-(3,4-dimethoxybenzyl)-5-oxo-4,5-dihydro-1,2,4-triazin-6-yl]ethyl}acetamide.

Yield: 15.5 g (77.5% of th.)

$^1$H-NMR (methanol-d$_4$): δ/ppm 1.40 (d, 3H), 1.95 (s, 3H), 3.78 (s, 3H), 3.81 (s, 3H), 3.82 (s, 2H), 5.16 (q, 1H), 6.86–6.97 (m, 3H).

EXAMPLE 15A 6-(1-Aminoethyl)-3-(3,4-dimethoxybenzyl)-1,2,4-triazin-5(4H)-one

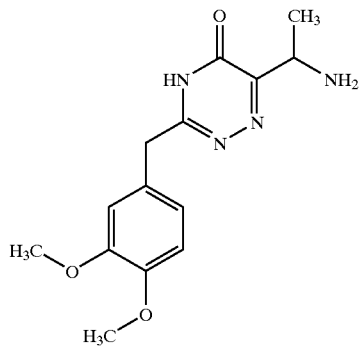

Analogously to Example 11A, 23 g of N-{1-[3-(3,4-dimethoxybenzyl)-5-oxo-4,5-dihydro-1,2,4-triazin-6-yl]ethyl}acetamide are reacted to give 6-(1-aminoethyl)-3-(3,4-dimethoxybenzyl)-1,2,4-triazin-5(4H)-one.

Yield: 10.1 g (50.4% of th.)

$^1$H-NMR (methanol-d$_4$): δ/ppm 1.55 (d, 3H), 3.78 (s, 3H), 3.80 (s, 3H), 3.83 (s, 2H), 4.52 (q, 1H), 6.83–6.98 (m, 3H).

EXAMPLE 16A

N-{1-[3-(3-Ethoxy-4-methoxybenzyl)-5-oxo-4,5-dihydro-1,2,4-triazin-6-yl]ethyl}acetamide

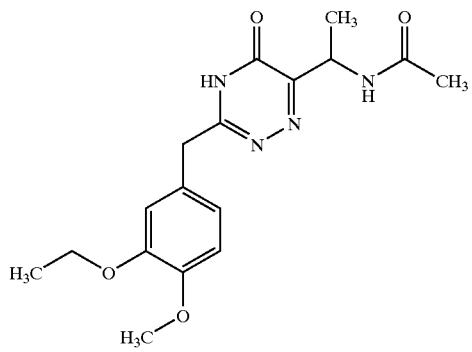

Analogously to Example 10A, 979 mg (4.00 mmol) of 2-(3-ethoxy-4-methoxyphenyl)ethanamidine hydrochloride are reacted with 200 mg (4.00 mmol) of hydrazine hydrate and 1.12 g (6.00 mmol) of ethyl 3-(acetylamino)-2-oxobutanoate to give N-{1-[3-(3,4-dimethoxybenzyl)-5-oxo-4,5-dihydro-1,2,4-triazin-6-yl]ethyl}acetamide.

Yield: 540 mg (38.2% of th.)

$^1$H-NMR (methanol-d$_4$): δ/ppm 1.37–1.41 (m, 6H), 1.94 (s, 3H), 3.80 (s, 3H), 3.82 (s, 2H), 4.05 (q, 2H), 5.11 (q, 1H), 6.85–6.96 (m, 3H).

EXAMPLE 17A 6-(1-Aminoethyl)-3-(3-ethoxy-4-methoxybenzyl)-1,2,4-triazin-5(4H)-one

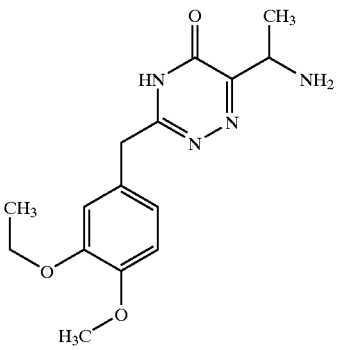

Analogously to Example 11A, 540 mg (1.56 mmol) of N-{1-[3-(3-ethoxy-4-methoxybenzyl)-5-oxo-4,5-dihydro-1,2,4-triazin-6-yl]ethyl}acetamide are reacted to give 6-(1-aminoethyl)-3-(3-ethoxy-4-methoxybenzyl)-1,2,4-triazin-5(4H)-one.

Yield: 491 mg (88.0% of th.)

$^1$H-NMR (methanol-d$_4$): δ/ppm 1.39 (t, 3H), 1.59 (d, 3H), 3.81 (s, 3H), 3.92 (s, 2H), 4.06 (q, 2H), 4.58 (q, 1H), 6.91–7.00 (m, 3H).

EXAMPLE 18A

N-{1-[3-(1-Naphthylmethyl)-5-oxo-4,5-dihydro-1,2,4-triazin-6-yl]ethyl}acetamide

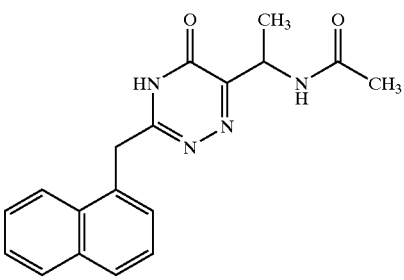

Analogously to Example 10A, 1.67 g (8.00 mmol) of 2-(1-naphthyl)ethanamidine hydrochloride are reacted with 401 mg (8.00 mmol) of hydrazine hydrate and 2.70 g (14.4 mmol) of ethyl 3-(acetylamino)-2-oxobutanoate to give N-{1-[3-(1-naphthylmethyl)-5-oxo-4,5-dihydro-1,2,4-triazin-6-yl]ethyl}acetamide.

Yield: 1.9 g crude yield

EXAMPLE 19A 6-(1-Aminoethyl)-3-(1-naphthylmethyl)-1,2,4-triazin-5(4H)-one

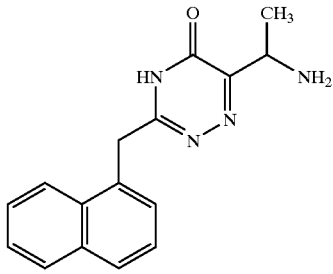

Analogously to Example 11A, 730 mg (2.26 mmol) of N-{1-[3-(1-naphthylmethyl)-5-oxo-4,5-dihydro-1,2,4-triazin-6-yl]ethyl}acetamide are reacted to give 6-(1-aminoethyl)-3-(1-naphthylmethyl)-1,2,4-triazin-5(4H)-one.

Yield: 655 mg (85.0% of th.)

Melting point: 180° C.

$^1$H-NMR (DMSO-d$_6$): δ/ppm 1.43 (d, 3H), 4.28–4.48 (q, 1H), 450 (s, 2H), 7.38–8.30 (m, 7H).

Example 20A

N-{1-[5-Oxo-3-(6-quinolinylmethyl)-4,5-dihydro-1,2,4-triazin-6-yl]ethyl}acetamide

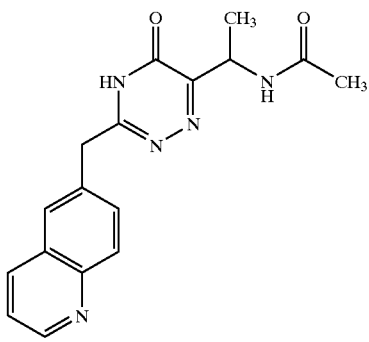

Analogously to Example 10A, 3.5 g (15.8 mmol) 2-(6-quinolinyl)ethanamidine hydrochloride are reacted with 950 mg (19.0 mmol) of hydrazine hydrate and 4.43 g (23.7 mmol) of ethyl 3-(acetylamino)-2-oxobutanoate to give N-{1-[5-oxo-3-(6-quinolinylmethyl)-4,5-dihydro-1,2,4-triazin-6-yl]ethyl}acetamide.

Yield: 3.4 g (55.2% of th.)

$^1$H-NMR (DMSO-d$_6$): δ/ppm 1.26 (d, 3H), 1.81 (s, 3H), 4.11 (s, 2H), 4.95 (q, 1H), 7.48–8.49 (m, 6H).

EXAMPLE 21A 6-(1-Aminoethyl)-3-(6-quinolinylmethyl)-1,2,4-triazin-5(4H)-one

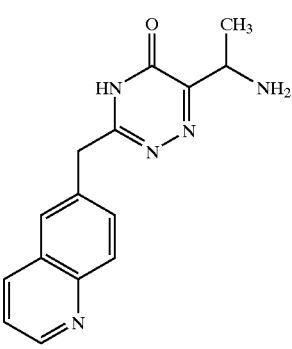

Analogously to Example 11A, 500 mg (1.55 mmol) of N-{1-[5-oxo-3-(6-quinolinylmethyl)-4,5-dihydro-1,2,4-triazin-6-yl]ethyl}acetamide are reacted to give 6-(1-aminoethyl)-3-(6-quinolinylmethyl)-1,2,4-triazin-5(4H)-one.

Yield: 360 mg (82.8% of th.)

$^1$H-NMR (DMSO-d$_6$): δ/ppm 1.38 (d, 3H), 3.95 (s, 2H), 4.24 (q, 1H), 7.46–8.84 (m, 6H).

EXAMPLE 22A

Ethyl 3-(acetylamino)-2-oxopentanoate

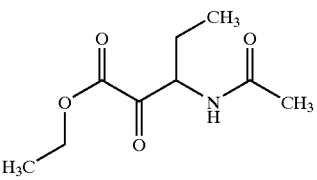

9.2 g (63.4 mmol) of acetyl-2-aminobutyric acid are taken up in 120 ml of tetrahydrofuran and heated to reflux with 15.0 g (190 mmol) of pyridine and a spatula tipful of N,N-dimethylaminopyridine. At boiling heat, 17.3 g (127 mmol) of ethyl oxalyl chloride are added dropwise. The mixture is then heated at reflux until evolution of gas can no longer be observed. After cooling, the batch is added to ice water and the organic phase is extracted in ethyl acetate. The dried organic phase is concentrated and, dissolved in ethanol, directly reacted further.

EXAMPLE 23A

N-{1-[3-(3,4-Dimethoxybenzyl)-5-oxo-4,5-dihydro-1,2,4-triazin-6-yl]propyl}-acetamide

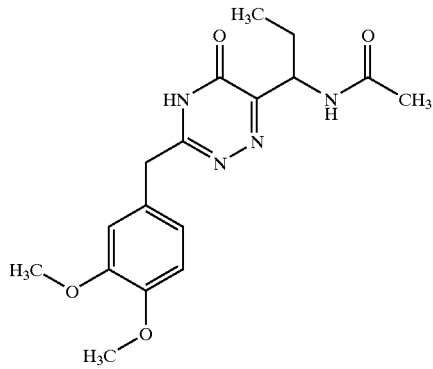

Analogously to Example 10A, 9.75 g (42.3 mmol) of 2-(3,4-dimethoxyphenyl)ethanamidine hydrochloride are reacted with 2.54 g (50.7 mmol) of hydrazine hydrate and 12.8 g (63.4 mmol) of ethyl 3-(acetylamino)-2-oxopentanoate to give N-{1-[3-(3,4-dimethoxybenzyl)-5-oxo-4,5-dihydro-1,2,4-triazin-6-yl]propyl}acetamide.

Yield: 2.05 g (14.0% of th.)

$^1$H-NMR (methanol-$d_4$): δ/ppm 0.96 (t, 3H), 1.63–1.99 (m, 2H), 1.96 (s, 3H), 3.80 (s, 3H), 3.82 (s, 3H), 3.84 (s, 2H), 4.98 (q, 1H), 6.86–6.97 (m, 3H).

EXAMPLE 24A 6-(1-Aminopropyl)-3-(3,4-dimethoxybenzyl)-1,2,4-triazin-5(4H)-one

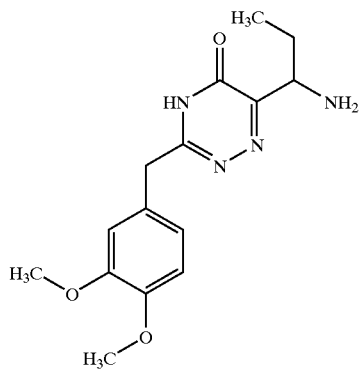

Analogously to Example 11A, 2.05 g (5.91 mmol) of N-{1-[3-(3,4-dimethoxybenzyl)-5-oxo-4,5-dihydro-1,2,4-triazin-6-yl]propyl}acetamide are reacted to give 6-(1-aminopropyl)-3-(3,4-dimethoxybenzyl)-1,2,4-triazin-5(4H)-one.

Yield: 2.15 g (67% of th.)

$^1$H-NMR (methanol-$d_4$): δ/ppm 1.02 (t, 3H), 1.90–2.13 (m, 2H), 3.80 (s, 3H), 3.83 (s, 3H), 3.86 (s, 2H), 4.44 (m, 1H), 6.91–6.70 (m, 3H).

EXAMPLE 25A

N-[1-(3-{4-Methyl-3-[(methylamino)sulphonyl]benzyl}-5-oxo-4,5-dihydro-1,2,4-triazin-6-yl)ethyl]acetamide

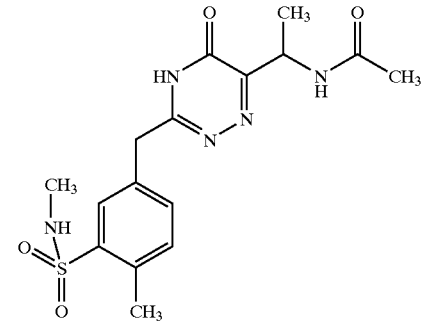

13.9 g (48.5 mmol) of N-{1-[3-(4-methylbenzyl)-5-oxo-4,5-dihydro-1,2,4-triazin-6-yl]ethyl}acetamide in 50 ml of dichloromethane are added dropwise to 56.6 g (485 mmol) of ice-cooled chlorosulphonic acid and the mixture is then stirred for 2 h, with warming to room temperature. The mixture is then added to 500 ml of dichloromethane/ice water 1:5 and the product is extracted in dichloromethane. The dried organic phase is treated with 55 ml of a 2M solution of methylamine in tetrahydrofuran and stirred for 10 min. It is then neutralized with 1N hydrochloric acid, concentrated and the residue is chromatographed using the eluent dichloromethane/methanol 20/1.

Yield: 8.25 g (44.8% of th.)

$^1$H-NMR (200 MHz, methanol-$d_4$): δ/ppm 1.40 (d, 3H), 1.94 (s, 3H), 2.49 (s, 3H), 2.58 (s, 3H), 3.97 (s, 2H), 5.04–5.17 (m, 1H), 7.33–7.92 (m, 3H).

EXAMPLE 26A

5-{[6-(1-Aminoethyl)-5-oxo-4,5-dihydro-1,2,4-triazin-3-yl]methyl}-N,2-dimethylbenzenesulphonamide

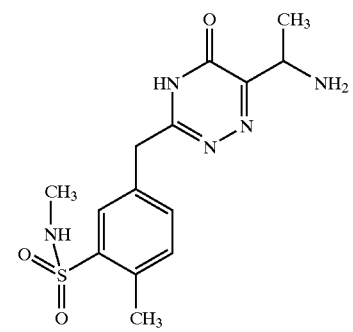

Analogously to Example 11A, 10.2 g (26.9 mmol) of N-[1-(3-{4-methyl-3-[(methylamino)sulphonyl]benzyl}-5-oxo-4,5-dihydro-1,2,4-triazin-6-yl)ethyl]acetamide are reacted to give 5-{[6-(1-aminoethyl)-5-oxo-4,5-dihydro-1,2,4-triazin-3-yl]methyl}-N,2-dimethylbenzenesulphonamide.

Yield: 4.4 g (48.5% of th.)

$^1$H-NMR (methanol-$d_4$): δ/ppm 1.55 (d, 3H), 2.51 (s, 3H), 2.57 (s, 3H), 3.97 (s, 2H), 4.54 (q, 1H), 7.27–7.89 (m, 3H).

EXAMPLE 27A

Sodium (2E)-4-methoxy-4-oxo-2-buten-2-olate

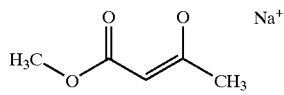

60 g of a 30% strength sodium hydride suspension in mineral oil (744 mmol of NaH) are suspended in 250 ml of dry THF in an inert gas atmosphere. 86.4 g (744 mmol) of methyl acetoacetate in 200 ml of THF are slowly added dropwise, the resulting hydrogen being led directly into the waste air. After dropwise addition has taken place, the mixture is stirred at reflux for half an hour and then cooled. The solvent is stripped off in vacuo and the residual solid is washed with diethyl ether.

Yield: 81.9 g (79.7% of th.)

Melting point: the substance decomposes at 200° C.

EXAMPLE 28A

Methyl-2-acetyl-5-phenylpentanoate

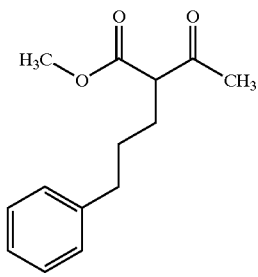

85 g (616 mmol) of sodium (2E)-4-methoxy-4-oxo-2-buten-2-olate suspended in 1,3-dimethyltetrahydro-2(1H)-pyrimidone and 3.50 g (21.1 mmol) of potassium iodide are treated dropwise with 129 g (646 mmol) of 1-bromo-3-phenylpropane and the mixture is stirred under reflux at 80° C. for 1 h. The cooled mixture is then added to ice water and extracted with diethyl ether. The ether phase is washed with sodium thiosulphate solution, dried, concentrated and chromatographed. The eluent used is cyclohexane containing an increasing proportion of ethyl acetate.

Yield: 57.0 g (39.5% of th.)

$^1$H-NMR (CDCl$_3$): δ/ppm 1.55–1.70 (m, 2H), 1.85–1.98 (m, 2H), 2.20 (s, 3H), 2.65 (t, 3H), 3.43 (t, 1H), 3.73 (s, 3H), 7.11–7.33 (m, 5H).

EXAMPLE 29A

2-Acetyl-5-phenylpentanoic Acid

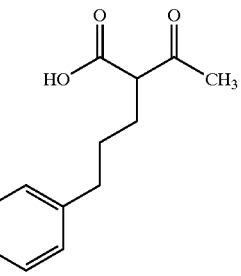

1.00 g (4.45 mmol) of methyl 2-acetyl-5-phenylpentanoate is dissolved in 10 ml of dioxane and cooled to 0° C. 8.5 ml of a 1 M sodium hydroxide solution are added with cooling. After a reaction time of 5 h, the batch is concentrated, treated with 10 ml of ethyl acetate and 10 ml of water and extracted by shaking. The water phase is recovered, cooled to 0° C. and slowly treated with 1 N hydrochloric acid with cooling until pH 1 is reached. It is then extracted with dichloromethane. The dichloromethane phase is dried and directly reacted further without concentrating.

Yield: 560 mg (59.6% of th.)

$^1$H-NMR (CDCl$_3$): δ/ppm 1.58–1.73 (m, 2H), 1.87–1.98 (m, 2H), 2.25 (s, 3H), 2.63 (t, 3H), 3.50 (t, 1H), 7.14–7.33 (m, 5H), 12.39 (s, COOH).

EXAMPLE 30A

Methyl 2-(1-hydroxyethyl)-5-phenylpentanoate

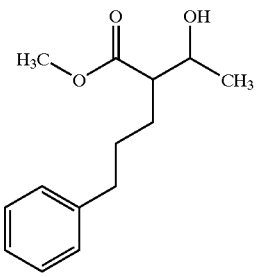

5.50 g (23.5 mmol) of methyl 2-acetyl-5-phenylpentanoate are introduced into 100 ml of methanol and the mixture is ice-cooled. 0.44 g (11.7 mmol) of sodium borohydride is added in portions and the mixture is stirred for a further 1 h. The solvent is then evacuated from the batch, and the residue is taken up in diethyl ether and washed with 1 N hydrochloric acid. The organic phase is then concentrated again and flash-chromatographed using the eluent petroleum ether/ethyl acetate 10/1.

Yield: 4.5 g (81.1% of th.)

$^1$H-NMR (CDCl$_3$, diastereomer mixture): δ/ppm 1.21 (d, 3H), 1.57–1.72 (m, 4H), 2.43 (m, 1H), 2.61 (t, 2H), 3.71 (s, 3H), 3.82–4.00 (m, 1H), 7.12–7.34 (m, 5H).

EXAMPLE 31A 2-(1-Hydroxyethyl)-5-phenylpentanoic Acid

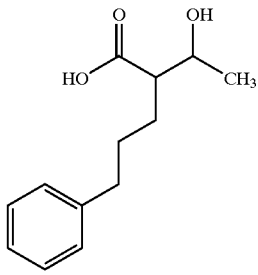

Analogously to Example 29A, 4.00 g (16.9 mmol) of methyl 2-(1-hydroxyethyl)-5-phenylpentanoate are reacted with 34.0 ml of a 1 M sodium hydroxide solution to give 2-(1-hydroxyethyl)-5-phenylpentanoic acid.

Yield: 3.56 g (94.6% of th.)

$^1$H-NMR (CDCl$_3$, diastereomer mixture): δ/ppm 1.18–1.30 (d, 3H), 1.56–1.83 (m, 4H), 2.36–2.50 (m, 1H), 2.57–2.71 (m, 2H), 3.89–4.02 (m, 1H), 7.11–7.33 (m, 5H).

EXAMPLE 32A

Methyl-(4E)-2-acetyl-5-phenyl-4-pentenoate

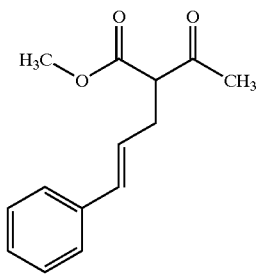

Analogously to Example 28A, 10 g (72.4 mmol) of sodium (2E)-4-methoxy-4-oxo-2-buten-2-olate and 0.40 g (2.41 mmol) of potassium iodide are reacted with 14.3 g (72.4 mmol) of [(1E)-3-bromo-1-propenyl]benzene to give methyl (4E)-2-acetyl-5-phenyl-4-pentenoate.

Yield: 8.30 g (49.4% of th.)
LC-MS: retention time 4.60 min., m/z 233 [M + H]$^+$
HPLC parameters  Soln. A acetonitrile
　　　　　　　　Soln. B 0.6 g 30% strength HCl/1 of water
　　　　　　　　Flow 0.6 ml/min.; column oven 50° C.;
　　　　　　　　Column Symmetry C18 2.1 × 150 mm

| Gradient: | time [min] | % A | % B | flow [ml/min] |
|---|---|---|---|---|
| | 0 | 10 | 90 | 0.6 |
| | 4 | 90 | 10 | 0.6 |
| | 9 | 90 | 10 | 0.8 |

EXAMPLE 33A

Methyl (4E)-2-(1-hydroxyethyl)-5-phenyl-4-pentenoate

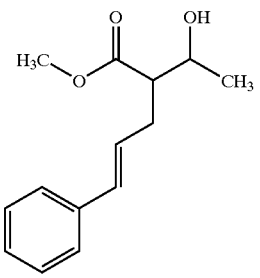

Analogously to Example 30A, 8.00 g (34.44 mmol) of methyl (4E)-2-acetyl-5-phenyl-4-pentenoate are reacted with 0.72 g (18.9 mmol) of sodium borohydride to give methyl (4E)-2-(1-hydroxyethyl)-5-phenyl-4-pentenoate.

Yield: 4.5 g (81.1% of th.)

Mass (DCI, NH$_3$): m/z=235 [M+H]$^+$, 252.1 [M+NH$_4$]$^+$.

EXAMPLE 34A (4E)-2-(1-Hydroxyethyl)-5-phenyl-4-pentenonoic Acid

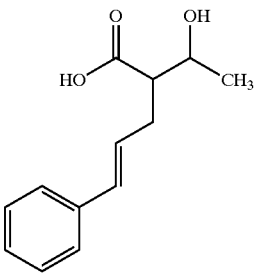

Analogously to Example 29A, 3.80 g (16.2 mmol) of methyl (4E)-2-(1-hydroxyethyl)-5-phenyl-4-pentenoate are reacted with 24.0 ml of a 1 M sodium hydroxide solution to give (4E)-2-(1-hydroxyethyl)-5-phenyl-4-pentenonoic acid.

Yield: 2.30 g (64.4% of th.)

$^1$H-NMR (CDCl$_3$): δ/ppm 1.26–1.35 (m, 3H), 2.49–2.71 (m, 3H), 3.98–4.17 (m, 1H), 6.11–6.26 (m, 1H), 6.33–6.54 (m, 1H), 7.17–7.37 (m, 5H).

EXAMPLE 35A

Methyl 2-acetyl-5-cyclohexylpentanoate

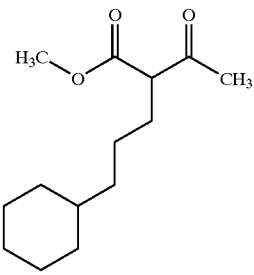

Analogously to Example 28A, 10 g (72.4 mmol) of sodium (2E)-4-methoxy-4-oxo-2-buten-2-olate and 0.4 g (2.41 mmol) of potassium iodide are reacted with 14.9 g (72.4 mmol) of (3-bromopropyl)cyclohexane to give methyl 2-acetyl-5-cyclohexylpentanoate.

Yield: 7.3 g (42.0% of th.)

$^1$H-NMR (CDCl$_3$): δ/ppm 0.73–0.98 (m, 2H), 1.04–1.41 (m, 8H), 1.53–1.92 (m, 7H), 2.20 (s, 3H), 3.42 (t, 1H), 3.74 (s, 3H).

EXAMPLE 36A

2-Acetyl-5-cyclohexylpentanoic Acid

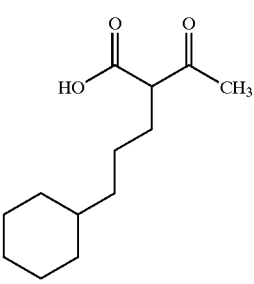

Analogously to Example 29A, 450 mg (2.08 mmol) of methyl 2-acetyl-5-cyclo-hexylpentanoate are reacted with 1.5 ml of a 3.5 M potassium hydroxide solution in dichloromethane to give 2-acetyl-5-cyclohexylpentanoic acid.

EXAMPLE 37A

Methyl 2-acetyl-2-methyl-5-phenylpentanoate

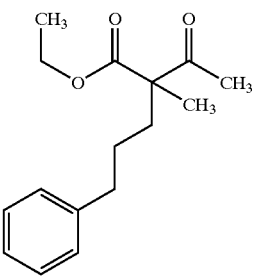

Analogously to Example 28A, 24 g (144 mmol) of sodium (2E)-4-methoxy-4-oxo-2-buten-2-olate and 0.70 g (4.22 mmol) of potassium iodide are reacted with 29.9 g (150 mmol) of 3-phenylpropyl bromide to give methyl 2-acetyl-2-methyl-5-phenylpentanoate.

Yield: 29.5 g (77.7% of th.)

$^1$H-NMR (CDCl$_3$): δ/ppm 1.23 (t, 3H), 1.32 (s, 3H), 1.42–1.60 (m, 2H), 1.70–1.98 (m, 2H), 2.09 (s, 3H), 2.62 (t, 2H), 4.17 (q, 2H), 7.12–7.32 (m, 5H).

EXAMPLE 38A

2-Acetyl-2-methyl-5-phenylpentanoic Acid

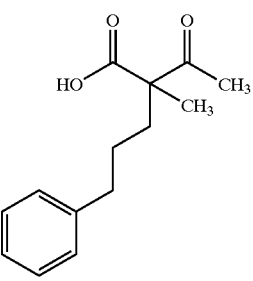

Analogously to Example 29A, 4.90 g (18.7 mmol) of methyl 2-acetyl-2-methyl-5-phenylpentanoate are reacted with 10.0 ml of a 3.5 M potassium hydroxide solution to give 2-acetyl-2-methyl-5-phenylpentanoic acid.

EXAMPLE 39A 2-(1-Hydroxyethyl)-N-{1-[3-(4-methylbenzyl)-5-oxo-4,5-dihydro-1,2,4-triazin-6-yl]-ethyl}-5-phenylpentanamide

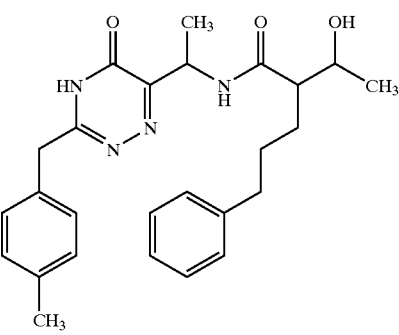

1.09 g (4.91 mmol) of 2-(1-hydroxyethyl)-5-phenylpentanoic acid are treated with 660 mg (4.61 mmol) of 1-hydroxy-1H-benzotriazole and 990 mg (9.82 mmol) of 4-methylmorpholine and the mixture is cooled to −20° C. After addition of 940 mg (4.61 mmol) of N'-(3-dimethylaminopropyl)-N-ethylcarbodiimide hydrochloride, the mixture is stirred for 30 min. At the same time, the cooling bath is removed. Then, after again cooling to −20° C., 1.00 g (4.09 mmol) of 6-(1-aminoethyl)-3-(4-methoxybenzyl)-1,2,4-triazin-5(4H)-one is added and the mixture is stirred overnight while warming to room temperature. For work-up, the dichloromethane phase is washed with 1N potassium hydrogensulphate solution and then with saturated sodium hydrogencarbonate solution. The dried organic phase is concentrated and chromatographed using the eluent dichloromethane/methanol 100/1 to 30/1.

Yield: 800 mg (44.8% of th.)

EXAMPLE 40A

2-Acetyl-N-{1-[3-(4-methylbenzyl)-5-oxo-4,5-dihydro-1,2,4-triazin-6-yl]ethyl}-5-phenylpentanamide

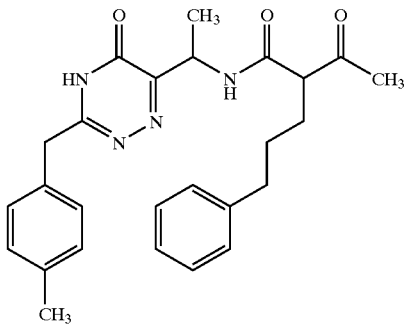

270 mg (2.14 mmol) of oxalyl chloride in 10 ml of dichloromethane are treated dropwise at −70° C. with 360 mg (4.64 mmol) of dimethyl sulphoxide. The mixture is stirred at −70° C. for 30 min, then 800 mg (1.78 mmol) of 2-(1-hydroxyethyl)-N-{1-[3-(4-methylbenzyl)-5-oxo-4,5-dihydro-1,2,4-triazin-6-yl]ethyl}-5-phenylpentanamide are added. After a further 30 min, during which the temperature in the batch rises to about −60° C., 900 mg (8.92 mmol) of triethylamine are added and the cooling bath is then removed. If the batch temperature has warmed almost to room temperature, 10 ml of water are added and, after stirring briefly, the phases are separated. The dried organic phase is chromatographed in dichloromethane/methanol 50/1.

Yield: 550 mg (69.1% of th.)

$^1$H-NMR (methanol-$d_4$, diastereomer mixture): δ/ppm 1.39–1.46 (m, 3H), 1.48–1.61 (m, 2H), 1.72–1.81 (m, 2H), 2.15 and 2.16 (each s, 3H), 2.30 (s, 3H), 2.55–2.64 (m, 2H), 3.47 (m, 1H), 3.84 and 3.85 (each s, 2H), 5.12 (m, 1H), 7.07–7.26 (m, 9H).

EXAMPLE 41A 2-(1-Hydroxyethyl)-N-{1-[3-(4-methoxybenzyl)-5-oxo-4,5-dihydro-1,2,4-triazin-6 yl]ethyl}-5-phenylpentanamide

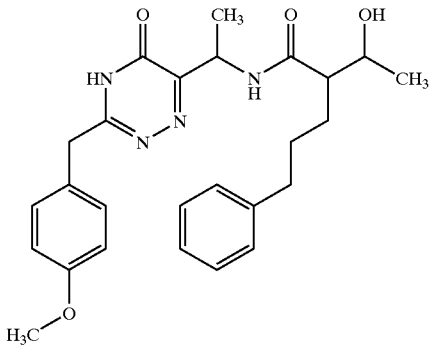

1.02 g (4.61 mmol) of 2-(1-hydroxyethyl)-5-phenylpentanoic acid are reacted analogously to Example 39A with 620 mg (4.61 mmol) of 1-hydroxy-1H-benzotriazole, 930 mg (9.22 mmol) of 4-methylmorpholine, 880 mg (4.61 mmol) of N'-(3-dimethylaminopropyl)-N-ethylcarbodiimide hydrochloride and 1.00 g (3.84 mmol) of 6-(1-aminoethyl)-3-(4-methoxybenzyl)-1,2,4-triazin-5(4H)-one to give 2-(1-hydroxyethyl)-N-{1-[3-(4-methoxybenzyl)-5-oxo-4,5-dihydro-1,2,4-triazin-6-yl]ethyl}-5-phenylpentanamide.

Yield: 800 mg (44.8% of th.)

LC-MS: Retention time 3.36, 3.46 and 3.56 min., m/z 465.4 [M + H]$^+$
LC parameters Soln. A acetonitrile + 0.1% formic acid
Soln. B water + 0.1% formic acid
Column oven 40° C.;
Column Symmetry C18 50 mm × 2.1 mm

| Gradient: | Time [min] | % A | % B | Flow [ml/min] |
|---|---|---|---|---|
| | 0 | 10 | 90 | 0.5 |
| | 4 | 90 | 10 | 0.5 |
| | 6 | 90 | 10 | 0.5 |
| | 6.1 | 10 | 90 | 1.0 |
| | 7.5 | 10 | 90 | 0.5 |
| | 9 | 90 | 10 | 0.8 |

EXAMPLE 42A

2-Acetyl-N-{1-[3-(4-methoxybenzyl)-5-oxo-4,5-dihydro-1,2,4-triazin-6-yl]ethyl}-5-phenylpentanamide

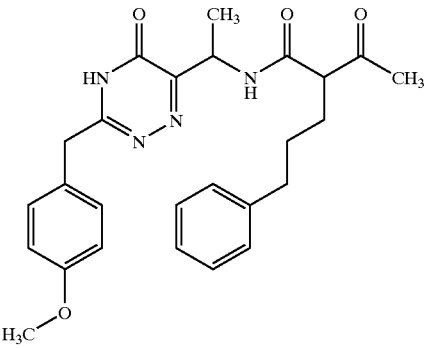

Analogously to Example 40A, 250 mg (1.94 mmol) of oxalyl chloride, 330 mg (4.2 mmol) of dimethyl sulphoxide, 750 mg (1.61 mmol) of 2-(1-hydroxyethyl)-N-{1-[3-(4-methoxybenzyl)-5-oxo-4,5-dihydro-1,2,4-triazin-6-yl]ethyl}-5-phenyl-pentanamide and 820 mg (8.07 mmol) of triethylamine are reacted to give 2-acetyl-N-{1-[3-(4-methoxybenzyl)-5-oxo-4,5-dihydro-1,2,4-triazin-6-yl]ethyl}-5-phenyl-pentanamide.

Yield: 320 mg (42.9% of th.)

$^1$H-NMR (methanol-$d_4$, diastereomer mixture): δ/ppm 1.44 (m, 3H), 1.48–1.61 (m, 2H), 1.71–1.82 (m, 2H), 2.15 (s, 3H), 2.54–2.64 (m, 2H), 3.46 (m, 1H), 3.75 (s, 3H), 3.82 (s, 2H), 5.14 (m, 1H), 6.82–7.28 (m, 9H).

EXAMPLE 43A 2-(1-Hydroxyethyl)-N-{1-[3-(3,4-dimethoxybenzyl)-5-oxo-4,5-dihydro-1,2,4-triazin-6-yl]ethyl}-5-phenylpentanamide

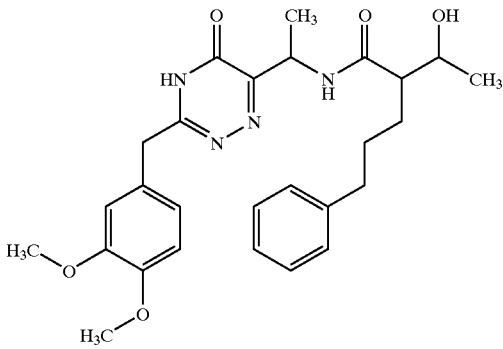

1.01 g (4.55 mmol) of 2-(1-hydroxyethyl)-5-phenylpentanoic acid are reacted analogously to Example 39A with 0.67 g (4.96 mmol) of 1-hydroxy-1H-benzotriazole, 1.05 g (10.3 mmol) of 4-methylmorpholine, 0.95 g (4.96 mmol) of N'-(3-dimethylaminopropyl)-N-ethylcarbodiimide hydrochloride and 1.20 g (4.13 mmol) of 6-(1-aminoethyl)-3-(3,4-dimethoxybenzyl)-1,2,4-triazin-5(4H)-one to give 2-(1-hydroxyethyl)-N-{1-[3-(3,4-dimethoxybenzyl)-5-oxo-4,5-dihydro-1,2,4-tri azin-6-yl]-ethyl)}5-phenylpentanamide.

Yield: 1.45 g (70.9% of th.)

$^1$H-NMR (methanol-$d_4$, diastereomer mixture): δ/ppm 1.10–1.18 (m, 3H). 1.40–1.46 (m, 3H), 1.51–1.65 (m, 4H), 2.19–2.29 (m, 1H), 2.50–2.66 (m, 2H), 3.77–3.84 (m, 9H), 5.12 (m, 1H), 6.86–7.25 (m, 8H).

EXAMPLE 44A

2-Acetyl-N-{1-[3-(3,4-dimethoxybenzyl)-5-oxo-4,5-dihydro-1,2,4-triazin-6-yl]-ethyl}-5-phenylpentanamide

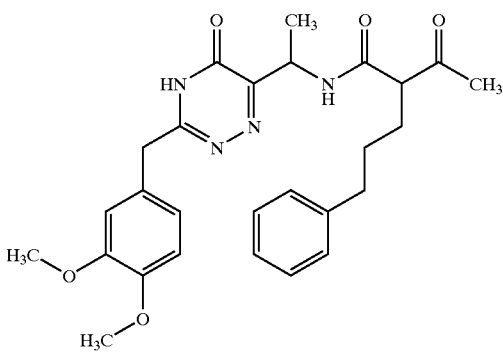

Analogously to Example 40A, 0.76 g (6.00 mmol) of oxalyl chloride, 1.01 g (12.9 mmol) of dimethyl sulphoxide, 1.95 g (3.93 mmol) of 2-(1-hydroxyethyl)-N-{1-[3-(3,4-dimethoxybenzyl)-5-oxo-4,5-dihydro-1,2,4-triazin-6-yl] ethyl}-5-phenyl-pentanamide and 4.36 g (43.1 mmol) of triethylamine are reacted to give 2-acetyl-N-{1-[3-(3,4-dimethoxybenzyl)-5-oxo-4,5-dihydro-1,2,4-triazin-6-yl]ethyl}-5-phenylpentanamide.

Yield: 1.30 g (67.2% of th.)

$^1$H-NMR (methanol-$d_4$, diastereomer mixture): δ/ppm 1.45 (m, 3H), 1.51–1.61 (m, 2H), 1.73–1.81 (m, 2H), 2.15 (s, 3H), 2.55–2.63 (m, 2H), 3.47 (m, 1H), 3.78–3.85 (m, 8H), 5.14 (m, 1H), 6.85–7.26 (m, 8H).

EXAMPLE 45A (4E)-N-{1-[3-(3,4-Dimethoxybenzyl)-5-oxo-4,5-dihydro-1,2,4-triazin-6-yl]ethyl}-2-(1-hydroxyethyl)-5-phenyl-4-pentenamide

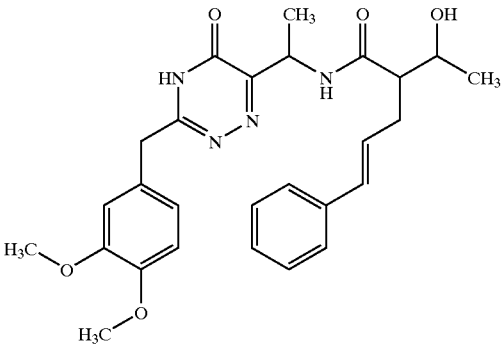

1.14 g (5.17 mmol) of (4E)-2-(1-hydroxyethyl)-5-phenyl-4-pentenonoic acid, are reacted analogously to Example 39A with 0.70 g (5.17 mmol) of 1-hydroxy-1H-benzotriazole, 1.05 g (10.3 mmol) of 4-methylmorpholine, 0.99 g (5.17 mmol) of N'-(3-dimethylaminopropyl)-N-ethylcarbodiimide hydrochloride and 0.60 g (2.07 mmol) of 6-(1-aminoethyl)-3-(3,4-dimethoxybenzyl)-1,2,4-triazin-5(4H)-one to give (4E)-N-{1-[3-(3,4-dimethoxybenzyl)-5-oxo-4,5-dihydro-1,2,4-triazin-6-yl]ethyl}-2-(1-hydroxyethyl)-5-phenyl-4-pentenamide.

Yield: 625 mg (61.4% of th.)

$^1$H-NMR (methanol-$d_4$, diastereomer mixture): δ/ppm 1.15–1.43 (m, 6H), 2.31–2.70 (m, 3H), 3.70–3.94 (m, 9H), 5.07–5.23 (m, 1H), 6.11–6.23 (m, 1H), 6.31–6.44 (m, 1H), 6.81–7.34 (m, 8H).

EXAMPLE 46A (4E)-2-Acetyl-N-{1-[3-(3,4-dimethoxybenzyl)-5-oxo-4,5-dihydro-1,2,4-triazin-6-yl]-ethyl}-5-phenyl-4-pentenamide

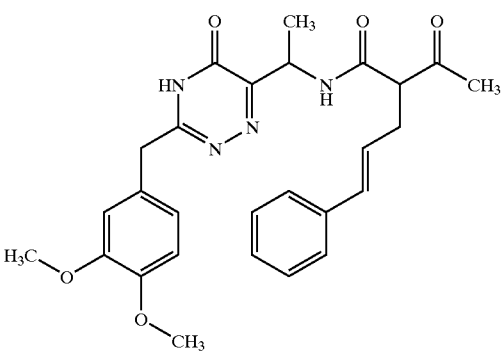

Analogously to Example 40A, 320 mg (2.50 mmol) of oxalyl chloride, 390 mg (5.00 mmol) of dimethyl sulphoxide, 800 mg (1.63 mmol) of (4E)-N-{1-[3-(3,4-dimethoxybenzyl)-5-oxo-4,5-dihydro-1,2,4-triazin-6-yl]

ethyl}-2-(1-hydroxyethyl)-5-phenyl-4-pentenamide and 1.82 g (18.0 mmol) of triethylamine are reacted to give (4E)-2-acetyl-N-{1-[3-(3,4-dimethoxybenzyl)-5-oxo-4,5-dihydro-1,2,4-triazin-6-yl]-ethyl}-5-phenyl-4-pentenamide.

Yield: 540 mg (67.5% of th.)

$^1$H-NMR (methanol-d$_4$, diastereomer mixture): δ/ppm 1.37 and 1.44 (each d, 3H), 2.20 and 2,21 (each s, 3H), 2.52–2.71 (m, 2H), 3.57–3.86 (m, 9H), 5.14 (m, 1H), 6.07–6.19 (m, 1H), 6.35–6.48 (m, 1H), 6.82–7.34 (m, 8H).

EXAMPLE 47A

2-Acetyl-5-cyclohexyl-N-{1-[3-(3,4-dimethoxybenzyl)-5-oxo-4,5-dihydro-1,2,4-triazin-6-yl]ethyl}pentanamide

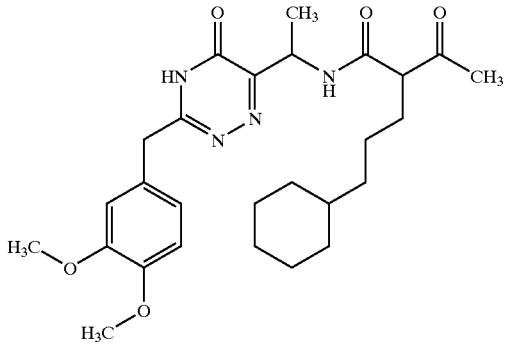

The amount of 2-acetyl-5-cyclohexylpentanoic acid in dichloromethane from Example 36A is reacted analogously to Example 39A with 280 mg (2.08 mmol) of 1-hydroxy-1H-benzotriazole, 610 mg (6.00 mmol) of 4-methylmorpholine, 400 mg (2.08 mmol) of N'-(3-dimethylaminopropyl)-N-ethylcarbodiimide hydrochloride and 600 mg (2.08 mmol) of 6-(1-aminoethyl)-3-(3,4-dimethoxybenzyl)-1,2,4-triazin-5(4H)-one to give 2-acetyl-5-cyclohexyl-N-{1-[3-(3,4-dimethoxybenzyl)-5-oxo-4,5-dihydro-1,2,4-triazin-6-yl]ethyl}pentanamide.

Yield: 248 mg (23.9% of th.) $^1$H-NMR (methanol-d$_4$, diastereomer mixture): δ/ppm 0.65–0.81 (m, 2H), 0.99–1.19 (m, 8H), 1.34 (d, 3H), 1.48–1.64 (m, 7H), 2.06 (s, 3H), 3.33 (m, 1H), 3.66–3.74 (m, 8H), 4.97–5.07 (m, 1H), 6.74–6.88 (m, 3H).

EXAMPLE 48A

2-Acetyl-N-{1-[3-(3,4-dimethoxybenzyl)-5-oxo-4,5-dihydro-1,2,4-triazin-6-yl]ethyl}-2-methyl-5-phenylpentanamide

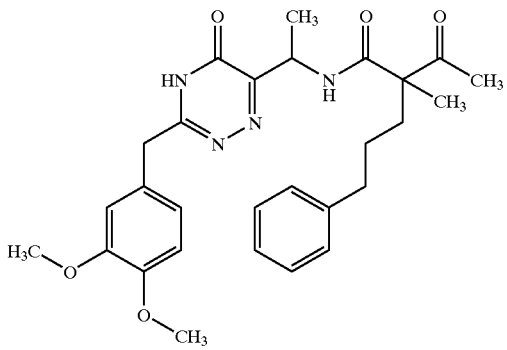

The amount of 2-acetyl-2-methyl-5-phenylpentanoic acid in 20 ml dichloromethane from Example 38A is reacted analogously to Example 39A with 300 mg (2.20 mmol) of 1-hydroxy-1H-benzotriazole, 670 mg (6.60 mmol) of 4-methylmorpholine, 420 mg (2.20 mmol) of N'-(3-dimethylaminopropyl)-N-ethylcarbodiimide hydrochloride and 620 mg (2.14 mmol) of 6-(1-aminoethyl)-3-(3,4-dimethoxybenzyl)-1,2,4-triazin-5(4H)-one to give 2-acetyl-N-{1-[3-(3,4-dimethoxybenzyl)-5-oxo-4,5-dihydro-1,2,4-triazin-6-yl]ethyl}-2-methyl-5-phenyl-pentanamide.

Yield: 544 mg (50.1% of th.)

$^1$H-NMR (methanol-d$_4$, diastereomer mixture): δ/ppm 1.19 (s, 3H), 1.28–1.41 (m, 5H), 1.60–1.81 (m, 2H), 1.96 and 1.97 (each s, 3H), 2.41–2.54 (m, 2H), 3.66–3.74 (m, 8H), 4.97–5.05 (m, 1H), 6.74–7.14 (m, 8H).

EXAMPLE 49A

N-{1-[3-(3,4-Dimethoxybenzyl)-5-oxo-4,5-dihydro-1,2,4-triazin-6-yl]propyl}-2-(1-hydroxyethyl)-5-phenylpentanamide

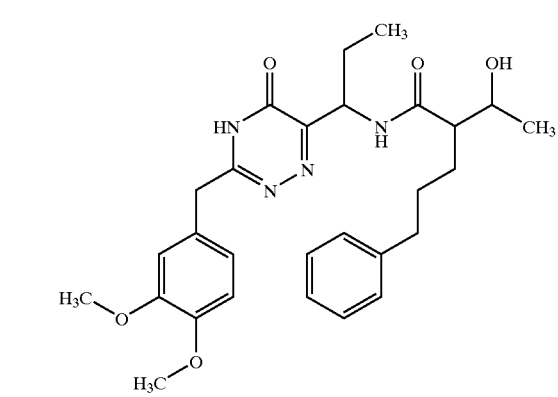

1.44 g (6.50 mmol) 2-(1-hydroxyethyl)-5-phenylpentanoic acid are reacted analogously to Example 39A with 1.00 g (6.50 mmol) of 1-hydroxy-1H-benzotriazole, 1.97 g (19.5 mmol) of 4-methylmorpholine, 1.25 g (6.350 mmol) of N'-(3-dimethylaminopropyl)-N-ethylcarbodiimide hydrochloride and 2.15 g (6.32 mmol) of 6-(1-aminopropyl)-3-(3,4-dimethoxybenzyl)-1,2,4-triazin-5(4H)-one to give N-{1-[3-(3,4-dimethoxybenzyl)-5-oxo-4,5-dihydro-1,2,4-triazin-6-yl]propyl}-2-(1-hydroxyethyl)-5-phenylpentanamide.

Yield: 881 mg (27.4% of th.)

$^1$H-NMR (methanol-d$_4$, diastereomer mixture): δ/ppm 0.90–1.03 (m, 3H), 1.09–1.20 (d, 3H), 1.46–1.99 (m, 6H), 2.25 (m, 1H), 2.49–2.66 (m, 2H), 3.66–3.86 (m, 9H), 5.01 (m, 1H), 6.83–7.26 (m, 8H).

EXAMPLE 50A

2-Acetyl-N-{1-[3-(3,4-dimethoxybenzyl)-5-oxo-4,5-dihydro-1,2,4-triazin-6-yl]-propyl}-5-phenylpentanamide

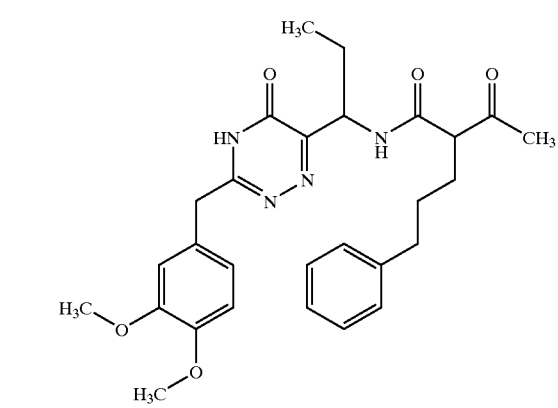

Analogously to Example 40A, 440 mg (305 mmol) of oxalyl chloride, 550 mg (7.00 mmol) of dimethyl sulphoxide, 920 mg (1.82 mmol) of N-{1-[3-(3,4-dimethoxybenzyl)-5-oxo-4,5-dihydro-1,2,4-triazin-6-yl]propyl}-2-(1-hydroxyethyl)-5-phenyl-pentanamide and 1.82 g (18 mmol) of triethylamine are reacted to give 2-acetyl-N-{1-[3-(3,4-dimethoxybenzyl)-5-oxo-4,5-dihydro-1,2,4-triazin-6-yl]propyl}-5-phenylpentanamide.

Yield: 537 mg (58.3% of th.)

$^1$H-NMR (methanol-$d_4$, diastereomer mixture): δ/ppm 0.93–1.05 (dt, 3H), 1.46–2.04 (m, 6H), 2.14 and 2.16 (each s, 3H), 2.51–2.67 (m, 2H,), 3.51 (m, 1H), 3.76–3.85 (m, 8H), 4.99 (m, 1H), 6.85–7.26 (m, 8H).

EXAMPLE 51A

N-{1-[3-(3-Ethoxy-4-methoxybenzyl)-5-oxo-4,5-dihydro-1,2,4-triazin-6-yl]propyl}2-(1-hydroxyethyl)-5-phenylpentanamide

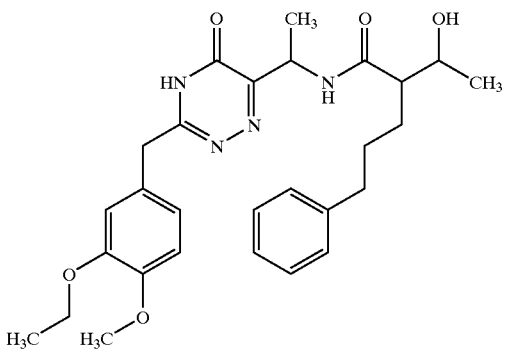

423 mg (1.90 mmol) of 2-(1-hydroxyethyl)-5-phenylpentanoic acid, are reacted analogously to Example 39A with 257 mg (1.90 mmol) of 1-hydroxy-1H-benzotriazole, 328 mg (2.54 mmol) of N-ethyldiisopropylamine, 365 mg (1.90 mmol) of N'-(3-dimethylaminopropyl)-N-ethylcarbodiimide hydrochloride and 432 mg (1.27 mmol) of 6-(1-aminopropyl)-3-(3-ethoxy-4-methoxybenzyl)-1,2,4-triazin-5(4H)-one to give N-{1-[3-(3-ethoxy-4-methoxybenzyl)-5-oxo-4,5-dihydro-1,2,4-triazin-6-yl]propyl}2-(1-hydroxyethyl)-5-phenylpentanamide.

Yield: 390 mg (56.9% of th.)

$^1$H-NMR (methanol-$d_4$, diastereomer mixture): δ/ppm 1.10–1.19 (m, 3H), 1.34–1.45 (m, 6H), 1.50–1.80 (m, 4H), 2.17–2.28 (m, 1H), 2.51–2.66 (m, 2H), 3.64–3.75 (m, 1H), 3.75–3.85 (m, 5H), 3.99–4.07 (m, 2H), 5.17 (m, 1H), 6.84–7.26 (m, 8H).

EXAMPLE 52A

2-Acetyl-N-{1-[3-(3-ethoxy-4-methoxybenzyl)-5-oxo-4,5-dihydro-1,2,4-triazin-6-yl]propyl}-5-phenylpentanamide

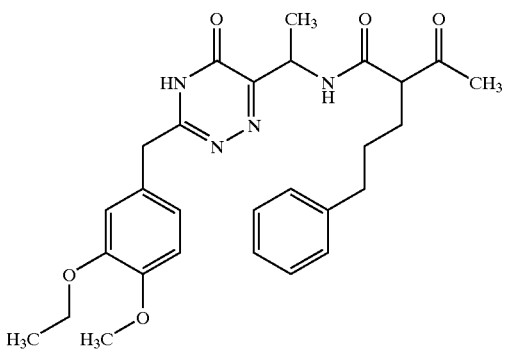

Analogously to Example 40A, 12.9 mg (0.10 mmol) of oxalyl chloride, 9.91 mg (0.13 mmol) of dimethyl sulphoxide, 43.0 mg (0.08 mmol) of N-{1-[3-(3-ethoxy-4-methoxybenzyl)-5-oxo-4,5-dihydro-1,2,4-triazin-6-yl]propyl}2-(1-hydroxyethyl)-5-phenylpentanamide and 32.8 mg (0.25 mmol) of N-ethyldiisopropylamine are reacted to give 2-acetyl-N-{1-[3-(3-ethoxy-4-methoxybenzyl)-5-oxo-4,5-dihydro-1,2,4-triazin-6-yl]propyl}-5-phenylpentanamide.

Yield: 40 mg (93.4% of th.)

$^1$H-NMR (methanol-$d_4$, diastereomer mixture): δ/ppm 1.22–1.36 (m, 6H), 1.38–1.50 (m, 2H), 1.54–1.67 (m, 2H), 2.08 (m, 3H), 2.45–2.60 (m, 2H, under DMSO signal), 3.47 (m, 1H), 3.72 (s, 3H), 3.75 (s, 2H), 3.92–4.02 (q, 2H), 4.90–5.06 (m, 1H), 6.79–7.30 (m, 8H).

EXAMPLE 53A 2-(1-Hydroxyethyl)-N-{1-[3-(1-naphthylmethyl)-5-oxo-4,5-dihydro-1,2,4-triazin-6-yl]ethyl}-5-phenylpentanamide

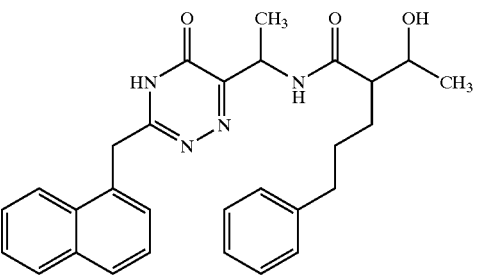

526 mg (2.37 mmol) of 2-(1-hydroxyethyl)-5-phenylpentanoic acid are reacted analogously to Example 39A with 320 mg (2.37 mmol) of 1-hydroxy-1H-benzotriazole, 408 mg (3.16 mmol) of N-ethyldiisopropylamine, 454 mg (6.350 mmol) of N'-(3-dimethylaminopropyl)-N-ethylcarbodiimide hydrochloride and 500 mg (1.58 mmol) of 6-(1-aminoethyl)-3-(1-naphthylmethyl)-1,2,4-triazin-5(4H)-one to give 2-(1-hydroxyethyl)-N-{1-[3-(1-naphthylmethyl)-5-oxo-4,5-dihydro-1,2,4-triazin-6-yl]ethyl}-5-phenylpentanamide.

Yield: 557 mg (66.3% of th.)

$^1$H-NMR (methanol-$d_4$, diastereomer mixture): δ/ppm 1.06–1.18 (m, 3H), 1.38–1.44 (m, 3H), 1.44–1.82 (m, 4H), 2.15–2.27 (m, 1H), 2.49–2.68 (m, 2H), 3.65–3.83 (m, 1H), 4.39 and 4.41 (s, 2H), 5.09–5.21 (m, 1H), 7.06–7.92 (m, 12H).

EXAMPLE 54A

2-Acetyl-N-{1-[3-(1-naphthylmethyl)-5-oxo-4,5-dihydro-1,2,4-triazin-6-yl]ethyl}-5-phenylpentanamide

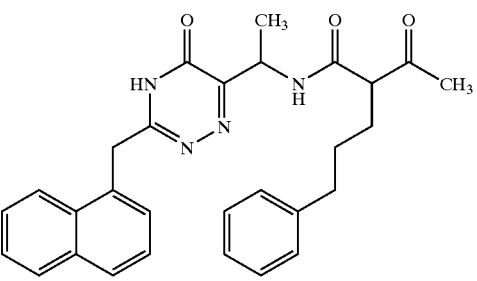

Analogously to Example 40, 310 mg (2.44 mmol) of oxalyl chloride, 239 mg (3.05 mmol) of dimethyl sulphoxide, 740 mg (1.53 mmol) of 2-(1-hydroxyethyl)-N-{1-[3-(1-naphthylmethyl)-5-oxo-4,5-dihydro-1,2,4-triazin-6-yl]ethyl}-5-phenyl-pentanamide and 790 mg (6.11 mmol) of N-ethyldiisopropylamine are reacted to give 2-acetyl-N-{1-[3-(1-naphthylmethyl)-5-oxo-4,5-dihydro-1,2,4-triazin-6-yl]ethyl}-5-phenylpentanamide.

Yield: 90 mg (12% of th.)

$^1$H-NMR (DMSO-d$_6$, diastereomer mixture): δ/ppm 1.19–1.71 (m, 7H), 2.07 (s, 3H), 2.45–2.61 (m, 2H, under DMSO signal), 3.46 (m, 1H), 4.37 (s, 2H). 4.91–5.01 (m, 1H), 7.10–8.16 (m, 12H).

EXAMPLE 55A

2-Acetyl-N-[1-(3-{4-methyl-3-[(methylamino)sulphonyl]benzyl 3–5-oxo-4,5-dihydro-12,4-triazin-6-yl)ethyl]-5-phenylpentanamide

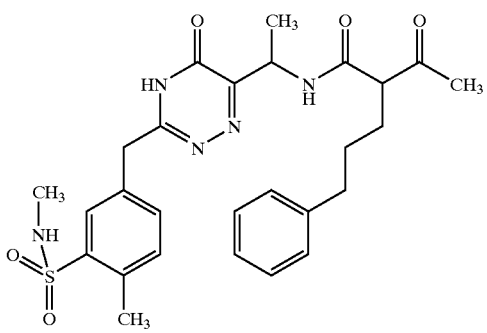

The amount of 2-acetyl-5-phenylpentanoic acid from Example 29A is reacted analogously to Example 39A with 600 mg (4.45 mmol) of 1-hydroxy-1H-benzotriazole, 410 mg (4.08 mmol) of 4-methylmorpholine, 850 mg (4.45 mmol) of N'-(3-dimethylaminopropyl)-N-ethylcarbodiimide hydrochloride and 1.25 g (3.70 mmol) of 5-{[6-(1-aminoethyl)-5-oxo-4,5-dihydro-1,2,4-triazin-3-yl]methyl}-N,2-dimethylbenzolsulphonamide to give 2-acetyl-N-[1-(3-{4-methyl-3-[(methyl-amino)sulphonyl]benzyl}-5-oxo-4,5-dihydro-12,4-triazin-6-yl)ethyl]-5-phenylpentan-amide.

Yield: 200 mg (10% of th.)

$^1$H-NMR (methanol-d$_4$, diastereomer mixture): δ/ppm 1.42 (d, 3H), 1.48–1.67 (m, 2H), 1.69–1.84 (m, 2H), 2.15 (s, 3H), 2.49 (s, 3H), 2.54–2.65 (m, 5H, s at 2.58), 3.48 (m, 1H), 3.97 (s, 2H), 5.12 (q, 1H), 7.06–7.89 (m, 8H).

Preparation Examples

EXAMPLE 1

7-(1-Acetyl-4-phenylbutyl)-5-methyl-2-(4-methylbenzyl)imidazo[5,1-f][1,2,4]triazin-4(3H)-one

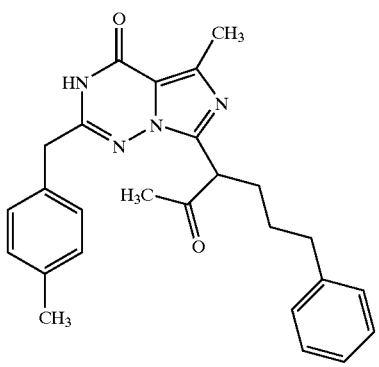

520 mg (1.16 mmol) of 2-acetyl-N-{1-[3-(4-methylbenzyl)-5-oxo-4,5-dihydro-1,2,4-triazin-6-yl]ethyl}-5-phenylpentanoic acid in 10 ml of dichloroethane are treated with 180 mg (1.16 mmol) of phosphorus oxychloride and stirred under reflux at 100° C. for 1 h. The cooled mixture is neutralized with saturated sodium hydrogencarbonate solution and the solvent is stripped off. The product is chromatographed using dichloromethane/methanol 70/1.

Yield: 300 mg (60.1% of th.)

Melting point (solid from diethyl ether): 119° C.

$^1$H-NMR (400 MHz, methanol-d$_4$): δ/ppm 1.45–1.54 (m, 2H), 2.00 (s, 3H), 2.00–2.13 (m, 2H), 2.28 (s, 3H), 2.53 (s, 3H), 2.53–2.60 (m, 2H), 3.78 (s, 2H), 4.31 (m, 1H), 7.05–7.22 (m, 9H).

EXAMPLE 2

7-(1-Acetyl-4-phenylbutyl)-2-(4-methoxybenzyl)-5-methylimidazo[5,1-f][1,2,4]triazin-4(3H)-one

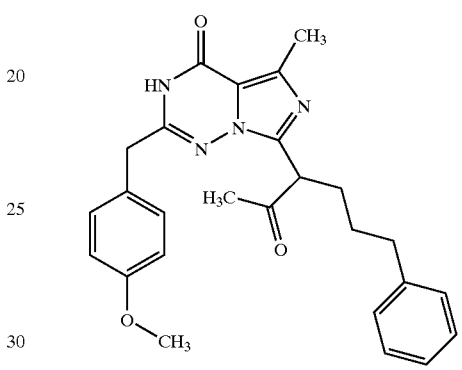

Analogously to Example 1, 290 mg (0.63 mmol) of 2-acetyl-N-1-[3-(4-methoxybenzyl)-5-oxo-4,5-dihydro-1,2,4-tri azin-6-yl]ethyl)}-5-phenylpentanamide and 100 mg (0.63 mmol) of phosphorus oxychloride are reacted to give 7-(1-acetyl-4-phenylbutyl)-2-(4-methoxybenzyl)-5-methylimidazo[5,1-f][1,2,4]triazin-4(3H)-one.

Yield: 155 mg (55.6% of th.)

Melting point (solid from diethyl ether): 138° C.

$^1$H-NMR (400 MHz, methanol-d4): δ/ppm 1.45–1.57 (m, 2H), 2.00 (s, 3H), 2.00–2.16 (m, 2H), 2.49–2.62 (m, 5H, s at 2.53), 3.74 (s, 3H), 3.76 (s, 2H), 4.32 (m, 1H), 6.83 (d, 2H), 7.08 (d, 2H), 7.08–7.23 (m, 5H).

EXAMPLE 3

7-(1-Acetyl-4-phenylbutyl)-2-(quinolin-6-ylmethyl)-5-methylimidazo[5,1-f][1,2,4]-triazin-4(3H)-one

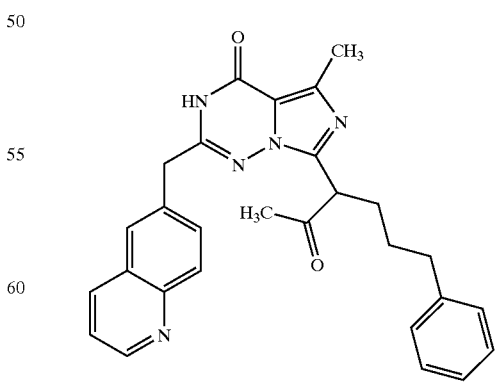

Analogously to Example 1,2-acetyl-N-{1-[3-(quinolin-6-ylmethyl)-5-oxo-4,5-dihydro-1,2,4-triazin-6-yl]ethyl}-5- phenylpentanamide and phosphorus oxychloride are reacted to give 7-(1-acetyl-4-phenylbutyl)-2-(quinolin-6-ylmethyl)-5-methylimidazo-[5,1-f][1,2,4]triazin-4(3H)-one.

$R_f$=0.60 (CH$_2$Cl$_2$: MeOH=10:1)

$^1$H-NMR (DMSO-d$_6$): δ/ppm 0.9–2.6 (m, 12H), 4.0–4.3 (m, 3H), 6.9–8.8 (m, 11H). MS: m/z=466 (M+H)

EXAMPLE 4

7-(1-Acetyl-4-phenylbutyl)-2-(3,4-dimethoxybenzyl)-5-methylimidazo[5,1-f][1,2,4]triazin-4(3H)-one

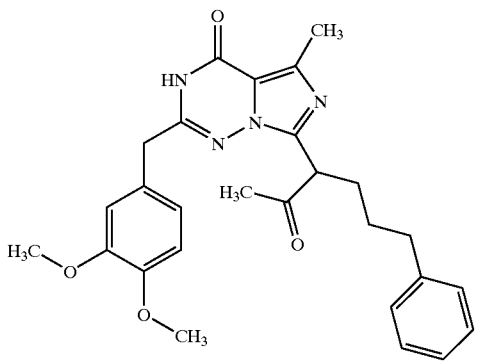

Analogously to Example 1, 1.30 g (2.64 mmol) of 2-acetyl-N-{1-[3-(3,4-dimethoxy-benzyl)-5-oxo-4,5-dihydro-1,2,4-triazin-6-yl]ethyl}-5-phenylpentanamide and 1.65 mg (10.7 mmol) of phosphorus oxychloride are reacted to give 7-(1-acetyl-4-phenylbutyl)-2-(3,4-dimethoxybenzyl)-5-methylimidazo[5,1-f][1,2,4]triazin-4(3H)-one.

Yield: 755 mg (60.2% of th.)

Melting point (solid from ethyl acetate/diethyl ether): 154° C.

$^1$H-NMR (400 MHz, methanol-d$_4$): δ/ppm 1.44–1.58 (m, 2H), 2.00 (s, 3H), 2.00–2.15 (m, 2H), 2.49–2.63 (m, 5H, s at 2.53), 3.76 (s, 2H), 3.78 (s, 6H), 4.30 (m, 1H), 6.85–7.21 (m, 8H).

EXAMPLE 5

7-[(3E)-1-Acetyl-4-phenyl-3-butenyl]-2-(3,4-dimethoxybenzyl)-5-methylimidazo-[5,1-f][1,2,4]triazin-4(3H)-one

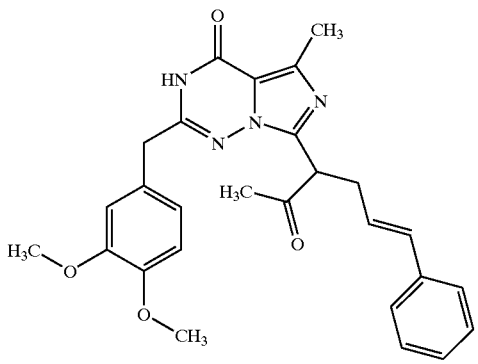

Analogously to Example 1, 540 mg (1.10 mmol) of (4E)-2-acetyl-N-{1-[3-(3,4-di-methoxybenzyl)-5-oxo-4,5-dihydro-1,2,4-triazin-6-yl]ethyl}-5-phenyl-4-pentenamide and 540 mg (3.50 mmol) of phosphorus oxychloride are reacted to give 7-[(3E)-1-acetyl-4-phenyl-3-butenyl]-2-(3,4-dimethoxybenzyl)-5-methylimidazo[5,1-f][1,2,4]-triazin-4(3H)-one.

Yield: 351 mg (67.7% of th.)

Rf (CH$_2$Cl$_2$/MeOH 10/1): 0.57

$^1$H-NMR (400 MHz, methanol-d$_4$): δ/ppm 2.06 (s, 3H), 2.53 (s, 3H), 2.85–3.02 (m, 2H), 3.77 (s, 2H), 3.79 (s, 6H), 4.48 (m, 1H), 6.06–6.14 (m, 1H), 6.28 (d, 1H), 6.84–7.23 (m, 8H).

EXAMPLE 6

7-(1-Acetyl-1-methyl-4-phenylbutyl)-2-(3,4-dimethoxybenzyl)-5-methylimidazo[5,1-f][1,2,4]triazin-4(3H)-one

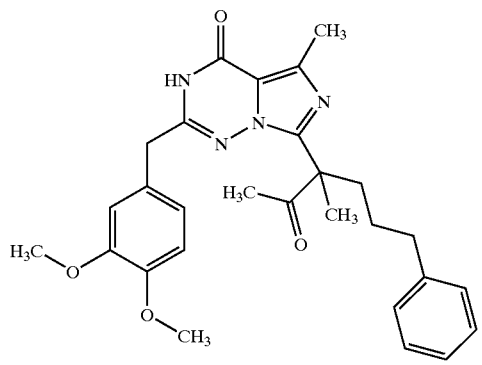

Analogously to Example 1, 3.08 g (6.07 mmol) of 2-acetyl-N-{1-[3-(3,4-dimethoxybenzyl)-5-oxo-4,5-dihydro-1,2,4-triazin-6-yl]ethyl}-2-methyl-5-phenylpentanamide and 4.44 mg (29.0 mmol) of phosphorus oxychloride are reacted to give 7-(1-acetyl-1-methyl-4-phenylbutyl)-2-(3,4-dimethoxybenzyl)-5-methylimidazo[5,1-f][1,2,4]-triazin-4(3H)-one.

Yield: 2.50 mg (84.2% of th.)

Rf (CH$_2$Cl$_2$/MeOH 10/1): 0.53

$^1$H-NMR (400 MHz, methanol-d$_4$): δ/ppm 1.10 and 1.57 (each m, 2H), 1.51 (s, 3H), 1.81 (s, 3H), 1.94 and 3.20 (each m, 2H), 2.38–2.58 (m, 5H, s at 2.54), 3.61 (s, 2H), 3.80 (s, 3H), 3.84 (s, 3H), 6.77–7.18 (m, 8H).

EXAMPLE 7

7-(1-Acetyl-4-cyclohexylbutyl)-2-(3,4-dimethoxybenzyl)-5-methylimidazo[5,1-f]-[1,2,4]triazin-4(3H)-one

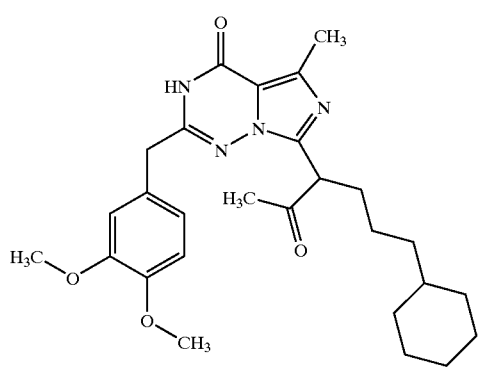

Analogously to Example 1, 240 mg (0.47 mmol) of 2-acetyl-5-cyclohexyl-N-{1-[3-(3,4-dimethoxybenzyl)-5- oxo-4,5-dihydro-1,2,4-triazin-6-yl]ethyl}pentanamide and 350 mg (2.30 mmol) of phosphorus oxychloride are reacted to give 7-(1-acetyl-4-cyclohexylbutyl)-2-(3,4-dimethoxybenzyl)-5-methylimidazo[5,1-f][1,2,4]triazin-4(3H)-one.

Yield: 147 mg (64.9% of th.)

Rf (CH$_2$Cl$_2$/MeOH 10/1): 0.46

$^1$H-NMR (400 NMz, methanol-d$_4$): δ/ppm 0.72–0.87 (m, 2H), 1.08–1.27 (m, 8H), 1.55–1.70 (m, 6H), 1.97–2.09 (m, 4H, s at 2.03), 2.54 (s, 3H), 3.78 (s, 2H), 3.81 (s, 3H), 3.83 (s, 3H), 4.27 (m, 1H), 6.87–6.97 (m, 3H).

EXAMPLE 8

7-(1-Acetyl-4-phenylbutyl)-2-(3,4-dimethoxybenzyl)-5-ethylimidazo[5,1-f][1,2,4]-triazin-4(3H)-one

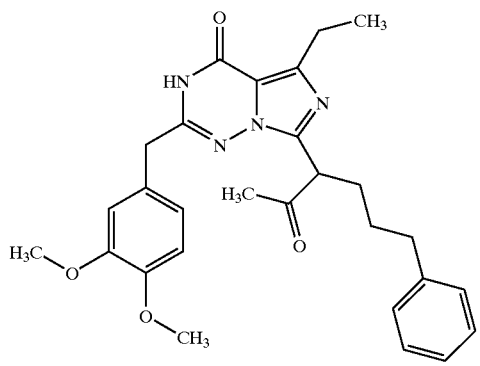

Analogously to Example 1, 530 mg (1.04 mmol) of 2-acetyl-N-{1-[3-(3,4-dimethoxybenzyl)-5-oxo-4,5-dihydro-1,2,4-triazin-6-yl]propyl}-5-phenylpentanamide and 610 mg (4.00 mmol) of phosphorus oxychloride are reacted to give 7-(1-acetyl-4-phenylbutyl)-2-(3,4-dimethoxybenzyl)-5-ethylimidazo[5,1-f][1,2,4]triazin-4(3H)-one.

Yield: 371 mg (73.1% of th.)

Rf (CH$_2$Cl$_2$/MeOH 10/1): 0.70

$^1$H-NMR (400 MHz, methanol-d$_4$): δ/ppm 1.26 (t, 3H), 1.42–1.58 (m, 2H), 2.00 (s, 3H), 2.00–2.15 (m, 2H), 2.50–2.66 (m, 2H), 2.94 (q, 2H), 3.76 (s, 2H), 3.78 (s, 6H), 4.31 (m, 1H), 6.85–7.23 (m, 8H).

EXAMPLE 9

7-(1-Acetyl-4-phenylbutyl)-2-(3-ethoxy-4-methoxybenzyl)-5-methylimidazo[5,1-f]-[1,2,4]triazin-4(3H)-one

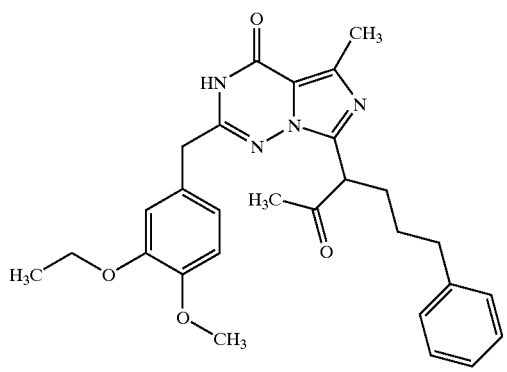

Analogously to Example 1, 123 mg (0.24 mmol) of 2-acetyl-N-{1-[3-(3-ethoxy-4-methoxybenzyl)-5-oxo-4,5-dihydro-1,2,4-triazin-6-yl]propyl}-5-phenylpentanamide and 41.0 mg (0.27 mmol) of phosphorus oxychloride are reacted to give 7-(1-acetyl-4-phenylbutyl)-2-(3-ethoxy-4-methoxybenzyl)-5-methylimidazo[5,1-f][1,2,4]triazin-4(3H)-one.

Yield: 52 mg (40.8% of th.)

Rf (CH$_2$Cl$_2$/MeOH 100/5): 0.48

$^1$H-NMR (400 MHz, methanol-d$_4$): δ/ppm 1.35 (t, 3H), 1.45–1.58 (m, 2H), 1.98–2.17 (m, 5H, s at 2.00), 2.49–2.63 (m, 5H, s at 2.53), 3.75 (s, 2H), 3.78 (s, 3H), 4.01 (q, 2H), 4.31 (m, 1H), 6.85–7.21 (m, 8H).

EXAMPLE 10

7-(1-Acetyl-4-phenylbutyl)-5-methyl-2-(1-naphthylmethyl)imidazo[5,1-f][1,2,4]-triazin-4(3H)-one

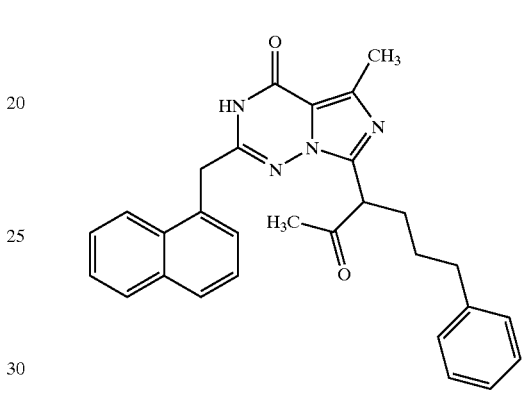

Analogously to Example 1, 80 mg (0.17 mmol) of 2-acetyl-N-{1-[3-(1-naphthylmethyl)-5-oxo-4,5-dihydro-1,2,4-triazin-6-yl]ethyl}-5-phenylpentanamide and 28.0 mg (0.18 mmol) of phosphorus oxychloride are reacted to give 7-(1-acetyl-4-phenylbutyl)-5-methyl-2-(1-naphthylmethyl)imidazo[5,1-f][1,2,4]triazin-4(3H)-one.

Yield: 10 mg (13.0% of th.)

Rf (CH$_2$Cl$_2$/MeOH 100/5): 0.48

$^1$H-NMR (400 MHz, methanol-d$_4$): δ/ppm 1.24–1.30 (m, 2H), 1.71 (s, 3H), 1.75–1.96 (m, 2H), 2.30–2.45 (m, 2H), 2.51 (s, 3H), 4.02 (m, 1H), 4.34 (s, 2H), 6.93–8.13 (m, 12H).

EXAMPLE 11

5-{[7-(1-Acetyl-4-phenylbutyl)-5-methyl-4-oxo-3,4-dihydroimidazo[5,1-f][1,2,4]triazin-2-yl]methyl}-N,2-dimethylbenzylsulphonamide

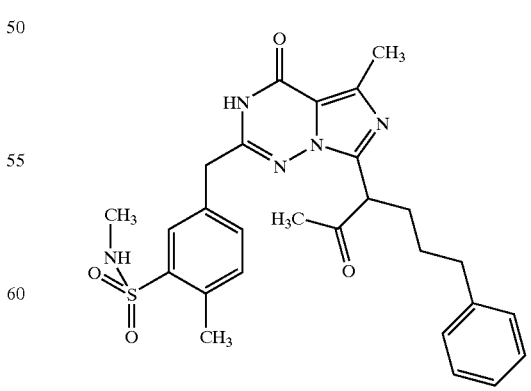

Analogously to Example 1, 250 mg (0.46 mmol) of 2-acetyl-N-[1-(3-{4-methyl-3-[(methylamino)sulphonyl]

benzyl}-5-oxo-4,5-dihydro-12,4-triazin-6-yl)ethyl]-5-phenylpentanamide and 0.32 mg (2.06 mmol) of phosphorus oxychloride are reacted to give 5-{[7-(1-acetyl-4-phenylbutyl)-5-methyl-4-oxo-3,4-dihydroimidazo[5,1-f]-[1,2,4]triazin-2-yl]methyl}-N,2-dimethylbenzolsulphonamide.

Yield: 110 mg (45.5% of th.)

¹H-NMR (200 MHz, methanol-d₄): δ/ppm 1.41–1.69 (m, 2H), 1.92–2.22 (m, 5H, s at 1.98), 2.44–2.63 (m, 11H, s at 2.48, 2.54 and 2.58), 3.89 (s, 2H), 4.25 (m, 1H), 7.03–7.95 (m, 8H).

EXAMPLE 12
7-[1-(1-Hydroxyethyl)-4-phenylbutyl]-5-methyl-2-(4-methylbenzyl)imidazo[5,1-f][1,2,4]triazin-4(3H)-one

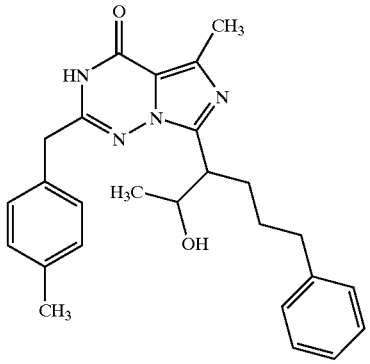

160 mg (0.37 mmol) of 7-(1-acetyl-4-phenylbutyl)-5-methyl-2-(4-methylbenzyl)-imidazo[5,1-f][1,2,4]triazin-4(3H)-one are dissolved in 5 ml of ethanol and treated in portions with 14 mg (0.37 mmol) of sodium borohydride. The batch is stirred at room temperature for 1 h, then neutralized using, a few drops of 2 N hydrochloric acid. The solvent is stripped off in vacuo, then the residue is chromatographed using the eluent dichloromethane/methanol 40/1.

Yield: 75 mg (46.7% of th.)

Melting point (solid from ether/cyclohexane): 143° C.

¹H-NMR (400 MHz, methanol-d₄, diastereomer mixture): δ/ppm 0.93 and 1.19 (each d, 3H), 1.26–1.44 (m, 2H), 1.69–2.14 (m, 2H), 2.27 (s, 3H), 2.42–2.62 (m, 5H, s at 2.52 and 2.53), 3.33–3.45 (m, 1H), 3.75 and 3.76 (each s, 2H), 3.97–4.11 (m, 1H) 6.98–7.22 (m, 9H).

EXAMPLE 13
7-[1-1-Hydroxyethyl)-4-phenylbutyl]-2-(quinolin-6-ylmethyl)-5-methylimidazo[5,1-f][1,2,4]triazin-4(3H)-one

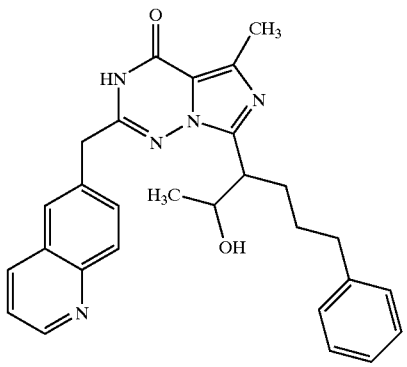

7-(1-Acetyl-4-phenylbutyl)-2-(quinolin-6-ylmethyl)-5-methylimidazo[5,1-f][1,2,4]-triazin-4(3H)-one is reacted analogously to Example 12 with sodium borohydride to give 7-[1-(1-hydroxyethyl)-4-phenylbutyl]-2-(quinolin-6-ylmethyl)-5-methylimidazo-[5,1-f][1,2,4]triazin-4(3H)-one.

R$_f$ (CH₂Cl₂/MeOH 10/1): 0.53

¹H-NMR (DMSO-d₆, diastereomer mixture): δ/ppm 0.9–2.6 (m, 12H), 3.3–3.7 (m, 1H), 3.9–4.1 (m, 3H), 6.9–8.8 (m, 11).

MS: m/z=468 (M+H).

EXAMPLE 14
7-[1-(1-Hydroxyethyl)-4-phenylbutyl]-2-(4-methoxybenzyl)-5-methylimidazo[5,1-f]-[1,2,4]triazin-4(3H)-one

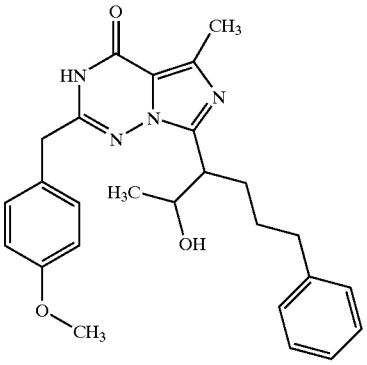

80 mg (0.19 mmol) of 7-(1-acetyl-4-phenylbutyl)-2-(4-methoxybenzyl)-5-methyl-imidazo[5,1-f][1,2,4]triazin-4(3H)-one are reacted analogously to Example 12 with 9 mg (0.19 mmol) of sodium borohydride to give 7-[1-(1-hydroxyethyl)-4-phenyl-butyl]-2-(4-methoxybenzyl)-5-methylimidazo[5,1-f][1,2,4]triazin-4(3H)-one.

Yield: 70 mg (82.0% of th.)

Rf (CH₂Cl₂/MeOH 10/1): 0.61

¹H-NMR (400 MHz, methanol-d₄, diastereomer mixture): δ/ppm 0.94 and 1.19 (each d, 3H), 1.28–1.44 (m, 2H), 1.70–2.14 (m, 2H), 2.42–2.63 (m, 5H, s at 2.53), 3.34–3.45 (m, 1H), 3.71–3.77 (m, 5H), 3.98–4.12 (m, 1H), 6.79 (d, 2H), 7.02 (d, 2H), 7.08–7.24 (m, 5H).

EXAMPLE 15
2-(3,4-Dimethoxybenzyl)-7-[1-(1-hydroxyethyl)-4-phenylbutyl]-5-methylimidazo-[5,1-f][1,2,4]triazin-4(3H)-one

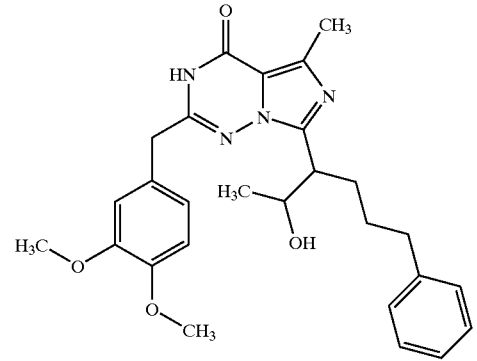

110 mg (0.22 mmol) of 7-(1-acetyl-4-phenylbutyl)-2-(3,4-dimethoxybenzyl)-5-methylimidazo[5,1-f][1,2,4]triazin-4

(3H)-one are reacted analogously to Example 12 with 20 mg (0.53 mmol) of sodium borohydride to give 2-(3,4-dimethoxybenzyl)-7-[1-(1-hydroxyethyl)-4-phenylbutyl]-5-methylimidazo[5,1-f][1,2,4]triazin-4(3H)-one.

Yield: 89 mg (84.4% of th.)

Rf (CH$_2$Cl$_2$/MeOH 10/1): 0.59

HPLC (RP 18, temp.: 40° C., flow 1.25 ml/min., 50% acetonitrile+water): Ratio of the diastereomers 33:60 (Example 16+17:Example 18+19)

$^1$H-NMR (400 MHz, methanol-d4, diastereomer mixture): δ/ppm 0.94 and 1.19 (each d, 3H), 1.28–1.45 (m, 2H), 1.70–2.15 (m, 2H), 2.41–2.61 (m, 5H, s at 2.53), 3.34–3.45 (m, 1H), 3.73–3.75 (m, 8H), 3.98–4.11 (m, 1H), 6.79–7.21 (m, 8H).

Example 15 is separated into the two diastereomeric compounds by chromatography under reversed phase conditions (Stability C30, 5 μm) using acetonitrile/water (1/1, v/v) as eluent. The corresponding enantiomerically pure compounds (Examples 16, 17, 18 and 19 below) can be obtained by chromatographic separation of the racemic diastereomers on a chiral stationary silica gel phase.

Particularly suitable chiral stationary polyamide silica gel phases (CSP) for the separation of the racemates are those based on the monomers N-methacryloyl-L-leucine-d-menthylamide or N-methacryloyl-L-leucine-l-menthylamide (cf. EP-A-0 379 917) using, for example, ethyl acetate as eluent.

The chromatographic resolution of the first-eluting diastereomers from Example 15 yields the two enantiomers Example 16 and Example 17. Analogously to this, the two enantiomers Example 18 and Example 19 are obtained from the later-eluting diastereomers.

EXAMPLE 16

2-(3,4-Dimethoxybenzyl)-7-{(1R)-1-[(1R)-1-hydroxyethyl]-4-phenylbutyl}-5-methylimidazo[5,1-f][1,2,4]triazin-4(3H)-one

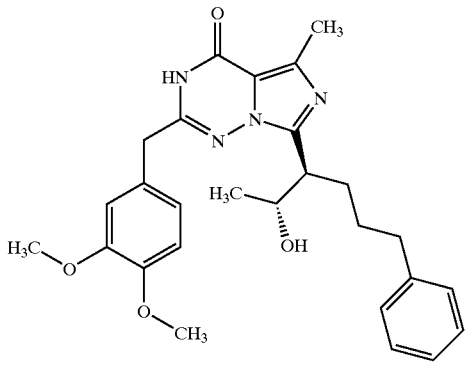

$^1$H-NMR (400 MHz, DMSO-d$_6$): δ/ppm 0.82 (d, 3H), 1.20–1.35 (m, 2H), 1.69–2.06 (m, 2H), 2.38–2.53 (m, 5H, s at 2.43, superimposed by DMSO signal), 3.17–3.25 (m, 1H), 3.65–3.72 (m, 8H), 3.78–3.88 (m, 1H), 4.79 (d, OH), 6.78–7.25 (m, 8H), 11.60 (s, NH).

[α]$^{20}_D$=−16.9° (c=0.41500 g/100 ml; solvent methanol)

Melting point: 167° C.

EXAMPLE 17

2-(3,4-Dimethoxybenzyl)-7-{(1S)-1-[(1S)-1-hydroxyethyl]-4-phenylbutyl}-5-methyl-imidazo[5,1-f][1,2,4]triazin-4(3H)-one

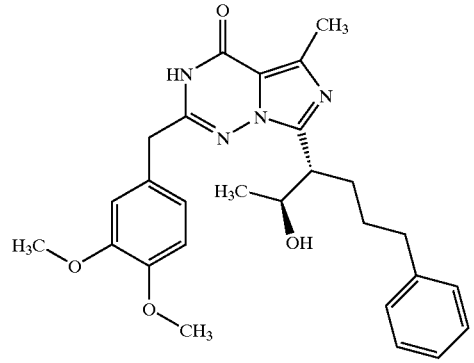

[α]$^{20}_D$=+18.4° (c=0.42500 g/100 ml; solvent methanol)

Melting point: 166° C.

The separation of the enantiomers Example 18 and Example 19 was carried out analogously to Example 16 starting from the later eluting diastereomer.

EXAMPLE 18

2-(3,4-Dimethoxybenzyl)-7-{(1R)-1-[(1S)-1-hydroxyethyl]-4-phenylbutyl}-5-methylimidazo[5,1-f][1,2,4]triazin-4(3H)-one

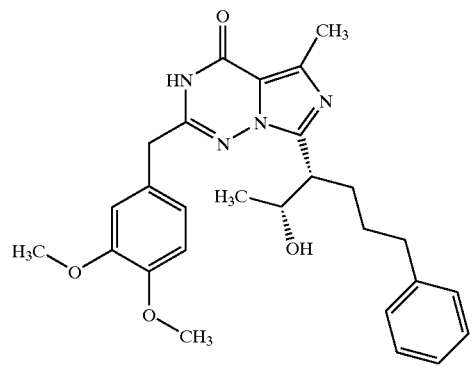

Characterization: [α]$^{20}_D$=+26.3° (c=0.44400 g/100 ml; solvent methanol)

Melting point: 167° C.

$^1$H-NMR (400 MHz, DMSO-d$_6$): δ/ppm 1.05 (d, 3H), 1.22–1.38 (m, 2H), 1.65–1.85 (m, 2H), 2.39–2.55 (m, 5H, s at 2.43, superimposed by DMSO signal), 3.26–3.35 (m, 1H), 3.66–3.72 (m, 8H), 3.88–3.97 (m, 1H), 4.54 (d, OH), 6.78–7.25 (m, 8H), 11.58 (s, NH).

EXAMPLE 19

2-(3,4-Dimethoxybenzyl)-7-{(1S)-1-[(1R)-1-hydroxyethyl]4-phenylbutyl}-5-methylimidazo[5,1-f][1,2,4]triazin-4(3H)-one

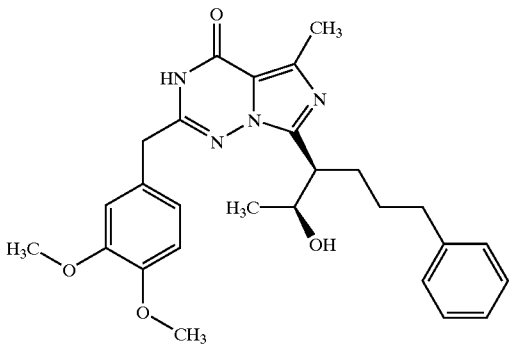

Characterization: $[\alpha]^{20}_D = -27.9°$ (c=0.45800 g/100 ml; solvent methanol)

Melting point: 167° C.

Moreover, the compounds of Examples 16 and 17 can also preferably be obtained by diastereoselective reduction of 7-(1-acetyl-4-phenylbutyl)-2-(3,4-dimethoxybenzyl)-5-methylimidazo[5,1-f][1,2,4]triazin-4(3H)-one.

For this, 190 mg (0.41 mmol) of 7-(1-acetyl-4-phenylbutyl)-2-(3,4-dimethoxy-benzyl)-5-methylimidazo[5,1-f][1,2,4]triazin-4(3H)-one are dissolved in 20 ml of dichloromethane/methanol 100/1 and, treated with 6.10 mg (0.45 mmol) of zinc chloride, stirred at room temperature for 30 min. After cooling to 0° C., 30 mg of sodium borohydride are added in portions and the mixture is then stirred for 2.5 h with ice-bath cooling. The batch is then neutralized using a few drops of 2 N hydrochloric acid, concentrated in vacuo and chromatographed using the eluent dichloromethane/methanol 80/1 and 40/1.

Yield: 158 mg (81.5% of th.) of diastereomer mixture

HPLC (RP 18, temp.: 40° C., flow 1.25 ml/min., 50% acetonitrile+water):ratio of the diastereomers 95:5 (Example 16+17:Example 18+19)

The diastereomer mixture is then purified under reversed phase chromatographic conditions as mentioned in Example 15 and separated into the pure enantiomers by chromatography on the chiral stationary phase.

EXAMPLE 20

2-(3,4-Dimethoxybenzyl)-7-[(3E)-1-(1-hydroxyethyl)-4-phenyl-3-butenyl]-5-methylimidazo[5,1-f][1,2,4]triazin-4(3H)-one

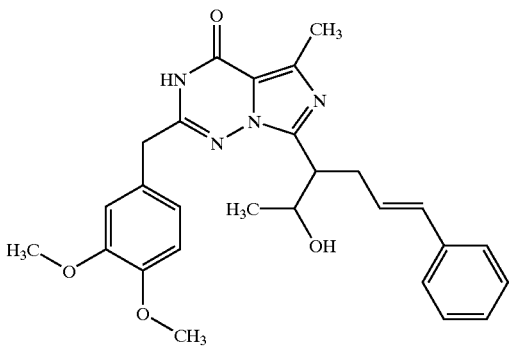

70 mg (0.14 mmol) of 7-[(3E)-1-acetyl-4-phenyl-3-butenyl]-2-(3,4-dimethoxy-benzyl)-5-methylimidazo[5,1-f][1,2,4]triazin-4(3H)-one are reacted analogously to Example 12 with 5 mg (0.14 mmol) of sodium borohydride to give 2-(3,4-dimethoxybenzyl)-7-[(3E)-1-1-hydroxyethyl)-4-phenyl-3-butenyl]-5-methylimidazo-[5,1-f][1,2,4]triazin-4 (3H)-one.

Yield: 55 mg (84.3% of th.)

Rf (CH$_2$Cl$_2$/MeOH 10/1): 0.40

$^1$H-NMR (400 MHz, methanol-d$_4$, diastereomer mixture): δ/ppm 1.02 and 1.27 (each d, 3H), 2.53 and 2.54 (each s, 2H), 2.65–2.78 (m, 2H), 3.49–3.60 (m, 1H), 3.74–3.80 (m, 8H), 4.10–4.24 (m, 1H), 5.95–6.04 (m, 1H), 6.16–6.25 (m, 1H), 6.78–7.19 (m, 8H).

EXAMPLE 21

2-(3,4-Dimethoxybenzyl)-7-[1-(1-hydroxyethyl)-1-methyl-4-phenoxybutyl]-5-methyl-imidazo[5,1-f][1,2,4]triazin-4(3H)-one

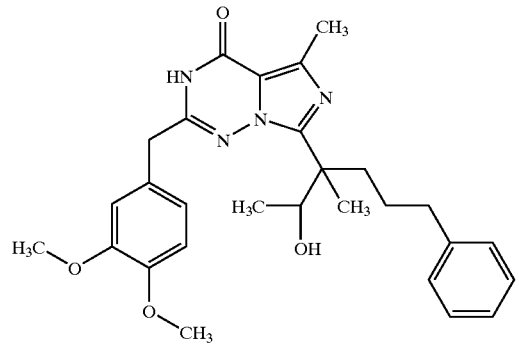

100 mg (0.20 mmol) of 7-(1-acetyl-1-methyl-4-phenylbutyl)-2-(3,4-dimethoxy-benzyl)-5-methylimidazo[5,1-f][1,2,4]triazin-4(3H)-one are reacted analogously to Example 12 with 23 mg (0.60 mmol) sodium borohydride to give 2-(3,4-dimethoxybenzyl)-7-[1-(1-hydroxyethyl)-1-methyl-4-phenylbutyl]-5-methylimidazo-[5,1-f][1,2,4]triazin-4(3H)-one.

Yield: 78 mg (77.7% of th.)

Rf (CH$_2$Cl$_2$/MeOH 10/1): 0.56

$^1$H-NMR (400 MHz, methanol-d$_4$, diastereomer mixture): δ/ppm 0.81 and 1.06 (each d, 3H), 0.84–1.01 and 1.39–1.55 (each m, 2H), 1.36 and 1.37 (each s, 3H), 1.73–2.16 (each m, 2H), 2.31–2.49 (m, 2H), 2.51 (s, 3H), 3.58–3.73 (m, 2H), 3.76–3.82 (m, 6H), 4.39–4.59 (m, 1H), 6.80–7.20 (m, 8H).

Example 21 is separated into the two diastereomeric compounds by chromatography under reversed phase conditions analogously to Example 15. The corresponding enantiomerically pure compounds (Examples 22, 23, 24, 25 below) can be obtained by chromatographic separation of the racemic diastereomers on a chiral stationary silica gel phase (see above).

EXAMPLE 22

Characterization: $[\alpha]^{20}_D = -69.1°$ (c=0.49750 g/100 ml; solvent methanol)

EXAMPLE 23

Characterization: $[\alpha]^{20}_D = -32.1°$ (c=0.34400 g/100 ml; solvent methanol)

EXAMPLE 24

$^1$H-NMR (400 MHz, methanol-d$_4$): δ/ppm 0.81 (d, 3H), 0.89–1.01 (m, 1H), 1.37 (s, 3H), 1.45–1.57 (m, 1H), 1.74–1.83 (m, 1H), 2.32–2.49 (m, 2H), 2.52 (s, 3H), 3.58–3.70 (m, 2H), 3.77–3.82 (m, 6H), 4.53–4.59 (m, 1H), 6.83–7.18 (m, 8H). Characterization: $[\alpha]^{20}_D = +73.3°$ (c=0.52850 g/100 ml; solvent methanol)

EXAMPLE 25

$^1$H-NMR (400 MHz, methanol-d$_4$): δ/ppm 1.06 (d, 3H), 0.85–0.97 (m, 1H), 1.37 (s, 3H), 1.40–1.50 (m, 2H), 2.08–2.18 (m, 1H), 2.31–2.49 (m, 2H), 2.52 (s, 3H), 3.62–3.75 (m, 2H), 3.78–3.82 (m, 6H), 4.38–4.44 (m, 1H), 6.81–7.20 (m, 8H).

Characterization: [α]$^{20}_D$=+31.0° (c=0.45600 g/100 ml; solvent methanol)

EXAMPLE 26

7-[4-Cyclohexyl-1-(1-hydroxyethyl)butyl]-2-(3,4-dimethoxybenzyl)-5-methylimidazo[5,1-f][1,2,4]triazin-4(3H)-one

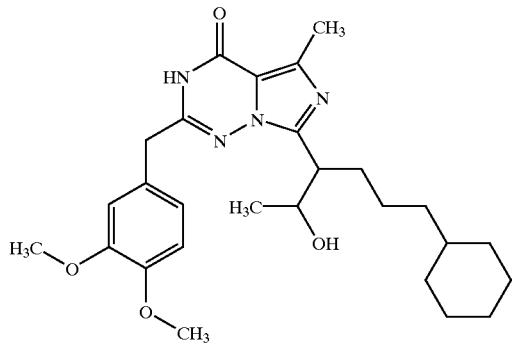

60 mg (0.13 mmol) of 7-(1-acetyl-4-cyclohexylbutyl)-2-(3,4-dimethoxybenzyl)-5-methylimidazo[5,1-f][1,2,4]triazin-4(3H)-one are reacted analogously to Example 12 with 15 mg (0.40 mmol) of sodium borohydride to give 7-[4-cyclohexyl-1-(1-hydroxyethyl)butyl]-2-(3,4-dimethoxybenzyl)-5-methylimidazo[5,1-f][1,2,4]triazin-4(3H)-one.

Yield: 52 mg (82.2% of th.)
Rf (CH$_2$Cl$_2$/MeOH 10/1): 0.39
$^1$H-NMR (400 MHz, methanol-c$_4$, diastereomer mixture): δ/ppm 0.66–0.92 (m, 2H), 0.93–1.24 (m, 11H), 1.48–2.07 (m, 7H), 2.54 (s, 3H), 3.33–3.41 (m, 1H), 3.77–3.84 (m, 8H), 3.98–4.12 (m, 1H), 6.89–6.99 (m, 3H).

EXAMPLE 27

2-(3,4-Dimethoxybenzyl)-5-ethyl-7-[1-(1-hydroxyethyl)-4-phenylbutyl]imidazo[5,1-f][1,2,4]triazin-4(3H)-one

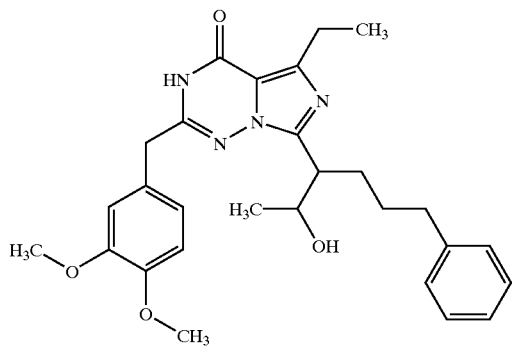

50 mg (0.10 mmol) of 7-(1-acetyl-4-phenylbutyl)-2-(3,4-dimethoxybenzyl)-5-ethyl-imidazo[5,1-f][1,2,4]triazin-4 (3H)-one, analogously to Example 12 are reacted with 19 mg (0.50 mmol) of sodium borohydride to give 2-(3,4-dimethoxybenzyl)-5-ethyl-7-[1-(1-hydroxyethyl)-4-phenylbutyl]imidazo[5,1-f][1,2,4]triazin-4(3H)-one.

Yield: 30 mg (59.8% of th.)
Rf (CH$_2$Cl$_2$/MeOH 10/1): 0.60
$^1$H-NMR (400 MHz, methanol-d$_4$, diastereomer mixture): δ/ppm 0.94 and 1.17 (each d, 3H), 1.21–1.30 (m, 3H), 1.31–1.43 (m, 2H), 1.68–2.13 (m, 2H), 2.39–2.61 (m, 2H), 2.89–2.99 (m, 2H), 3.35–3.46 (m, 1H), 3.72–3.79 (m, 8H), 4.01–4.14 (m, 1H), 6.79–7.21 (m, 8H).

EXAMPLE 28

2-(3-Ethoxy-4-methoxybenzyl)-7-[1-(1-hydroxyethyl)-4-phenylbutyl]-5-methylimidazo[5,1-f][1,2,4]triazin-4(3H)-one

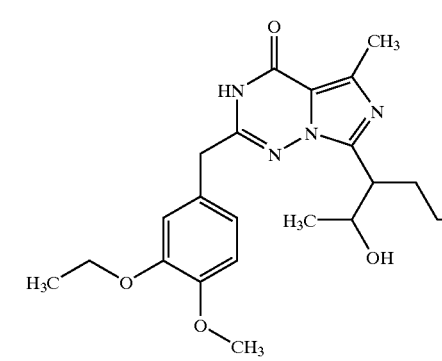

58 mg (0.12 mmol) of 7-(1-acetyl-4-phenylbutyl)-2-(3-ethoxy-4-methoxybenzyl)-5-methylimidazo[5,1-f][1,2,4]triazin-4(3H)-one are reacted analogously to Example 12 with 5 mg (0.12 mmol) of sodium borohydride to give 2-(3-ethoxy-4-methoxybenzyl)-7-[1-(1-hydroxyethyl)-4-phenylbutyl]-5-methylimidazo[5,1-f]-[1,2,4]triazin-4(3H)-one.

Yield: 56 mg (96.2% of th.)
Rf (CH$_2$Cl$_2$/MeOH 100/5): 0.23
$^1$H-NMR (400 MHz, DMSO-d$_6$, diastereomer mixture): δ/ppm 0.82 and 1.05 (each d, 3H), 1.22–1.35 (m, 5H), 1.66–2.05 (m, 2H), 2.40–2.55 (m, 5H, s at 2.42 and 2.43), 3.17–3.24 (m, 1H), 3.66 (s, 2H), 3.68 (s, 3H), 3.79–3.85 (m, 1H), 3.90–3.98 (m, 2H), 6.78–7.24 (m, 8H).

EXAMPLE 29

5-({7-[1-(1-Hydroxyethyl)-4-phenylbutyl]-5-methyl-4-oxo-3,4-dihydroimidazo[5,1-f][1,2,4]triazin-2-yl}methyl)-N,2-dimethylbenzylsulphonamide

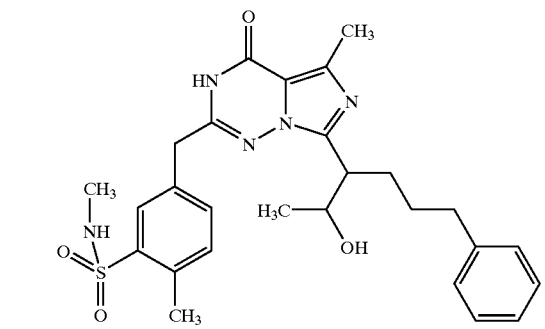

100 mg (0.19 mmol) of 5-{[7-(1-acetyl-4-phenylbutyl)-5-methyl-4-oxo-3,4-dihydro-imidazo[5,1-f][1,2,4]triazin-2- yl]methyl}-N,2-dimethylbenzylsulphonamide are reacted analogously to Example 12 with 7.2 mg (0.19 mmol) of sodium borohydride to give 5-({7-[1-(1-hydroxyethyl)-4-phenylbutyl]-5-methyl-4-oxo-3,4-dihydroimidazo[5,1-f][1,2,4]triazin-2-yl}methyl)-N,2-dimethylbenzylsulphonamide.

Yield: 59 mg (57.4% of th.)

$^1$H-NMR (400 MHz, methanol-$d_4$, diastereomer mixture): δ/ppm 0.92 and 1.15 (each d, 3H), 1.27–1.43 (m, 2H), 1.64–2.10 (m, 2H), 2.38–2.59 (m, 11H), 3.25–3.46 (m, 1H), 3.88 (s, 2H), 3.96–4.07 (m, 1H), 6.98–7.93 (m, 8H).

What is claimed is:

1. A compound of the formula

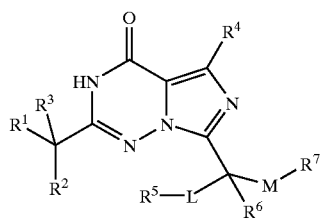

(I)

in which $R^1$ denotes phenyl, naphthyl, quinolinyl or isoquinolinyl, each of which can be substituted up to three times identically or differently by radicals selected from the group consisting of $(C_1–C_4)$-alkyl, $(C_1–C_4)$-alkoxy, halogen, cyano, —NHCOR$^8$, —NHSO$_2$R$^9$, —SO$_2$NR$^{10}$R$^{11}$, —SO$_2$R$^{12}$, and —NR$^{13}$R$^{14}$, in which $R^8$, $R^{10}$, $R^{11}$, $R^{13}$ and $R^{14}$ independently of one another are hydrogen or $(C_1–C_4)$-alkyl, and $R^9$ and $R^{12}$ independently of one another are $(C_1–C_4)$-alkyl, or $R^{10}$ and $R^{11}$ together with the adjacent nitrogen atom form an azetidin-1-yl, pyrrol-1-yl, piperid-1-yl, azepin-1-yl, 4-methyl-piperazin-1-yl or morpholin-1-yl radical, or $R^{13}$ and $R^{14}$ together with the adjacent nitrogen atom form an azetidin-1-yl, pyrrol-1-yl, piperid-1-yl, azepin-1-yl, 4-methyl-piperazin-1-yl or morpholin-1-yl radical, $R^2$ and $R^3$ independently of one another denote hydrogen or fluorine, $R^4$ denotes $(C_1–C_4)$-alkyl, $R^5$ denotes $(C_1–C_3)$-alkyl, $R^6$ denotes hydrogen or methyl, $R^7$ denotes phenyl, thiophenyl, furanyl, each of which can be substituted up to three times identically or differently by radicals selected from the group consisting of $(C_1–C_4)$-alkyl, $(C_1–C_4)$-alkoxy, halogen and cyano, or denotes $(C_5–C_8)$-cycloalkyl, L denotes carbonyl or hydroxymethanediyl, and M denotes $(C_2–C_5)$-alkanediyl, $(C_2–C_5)$-alkenediyl or alkinediyl, or a physiologically tolerable salt thereof.

2. The compound according to claim 1, where $R^1$ denotes phenyl, whose meta and/or para positions are substituted up to three times identically or differently by radicals selected from the group consisting of $(C_1–C_4)$-alkyl, $(C_1–C_4)$-alkoxy and —SO$_2$NR$^{10}$R$^{11}$, and $R^{10}$ and $R^{11}$ have the meaning indicated in claim 1.

3. The compound according to claim 1 or 2, where $R^7$ denotes phenyl.

4. The compound according to claim 1, where $R^1$ denotes phenyl, whose meta and/or para positions are substituted up to three times identically or differently by radicals selected from the group consisting of $(C_1–C_4)$-alkyl, $(C_1–C_4)$-alkoxy, —SO$_2$NR$^{10}$R$^{11}$, naphthyl and quinolinyl, in which $R^{10}$ and $R^{11}$ independently of one another are hydrogen or $(C_1–C_4)$-alkyl, $R^1$ and $R^2$ denote hydrogen, $R^4$ denotes methyl or ethyl, $R^5$ denotes methyl, $R^6$ denotes hydrogen or methyl, L denotes carbonyl or hydroxymethanediyl, and M denotes straight-chain $(C_2–C_5)$-alkane-1,ω-diyl, straight-chain $(C_2–C_5)$-alkene-1,ω-diyl or straight-chain $(C_2–C_5)$-alkine-1,ω-diyl or straight-chain $(C_2–C_5)$-alkine-1,ω-diyl.

5. Process for the preparation of compounds of the formula (I) according to claim 1, where (A) a compound of the formula (IIa),

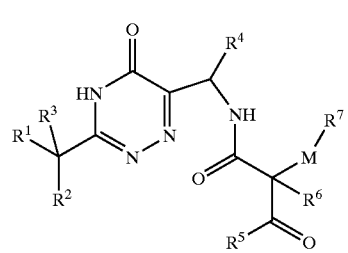

(IIa)

in which $R^1$, $R^2$, $R^3$, $R^4$, $R^5$, $R^6$ and $R^7$ and M have the meaning indicated in claim 1, is reacted under suitable condensation conditions to give a compound of the general formula (Ia),

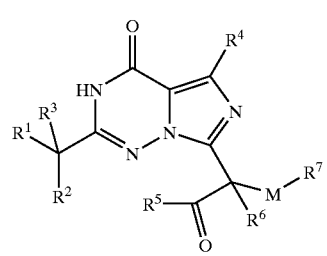

(Ia)

in which $R^1$, $R^2$, $R^3$, $R^4$, $R^5$, $R^6$, $R^7$ and M have the meaning indicated in claim 1, and then, optionally, (B) is reduced under suitable conditions to give a compound of the formula (Ib)

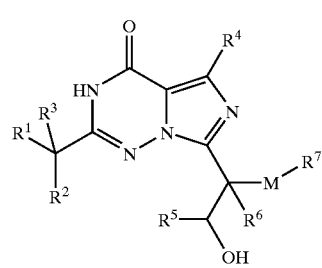

(Ib)

in which $R^1$, $R^2$, $R^3$, $R^4$, $R^5$, $R^6$, $R^7$ and M have the meaning indicated in claim 1.

6. A compound of the formula (II)

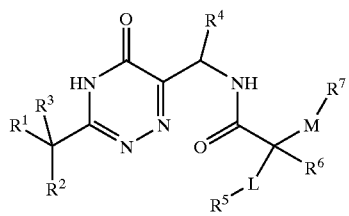

in which $R^1$, $R^2$, $R^3$, $R^4$, $R^5$, $R^6$, $R^7$, L and M have the meaning indicated in claim 1, or a physiologically tolerable salt thereof.

7. A pharmaceutical composition comprising a compound according to claim 1 and a pharmaceutically acceptable carrier.

8. A method for prophylaxis or treatment of a disorder of perception, concentration power, learning power and/or memory power, comprising administering to a subject in need thereof an effective amount of a compound according to claim 1.

9. The method of claim 8 wherein the disorder is a result of dementia.

10. A method of treatment to improve perception, concentration power, learning power, and/or memory power, comprising administering to a subject in need thereof an effective amount of a compound according to claim 1.

11. A method for prophylaxis or treatment of dementia comprising administering to a subject in need thereof an effective amount of a compound according to claim 1.

* * * * *